(12) United States Patent
Mitsis et al.

(10) Patent No.: US 7,892,797 B2
(45) Date of Patent: Feb. 22, 2011

(54) SINGLE ENZYME SYSTEM FOR FAST, ULTRA LONG PCR

(75) Inventors: Paul Mitsis, Trenton, NJ (US);
Anuradha Sekher, Belle Mead, NJ (US); Gyanendra Kumar, Franklin Park, NJ (US)

(73) Assignee: GE Healthcare Bio-Sciences Corp., Piscataway, NJ (US)

( * ) Notice: Subject to any disclaimer, the term of this patent is extended or adjusted under 35 U.S.C. 154(b) by 0 days.

(21) Appl. No.: 12/115,198

(22) Filed: May 5, 2008

(65) Prior Publication Data

US 2009/0170167 A1   Jul. 2, 2009

Related U.S. Application Data

(60) Provisional application No. 61/016,850, filed on Dec. 27, 2007, provisional application No. 61/025,047, filed on Jan. 31, 2008.

(51) Int. Cl.
*C12Q 1/68* (2006.01)
*C12P 19/34* (2006.01)

(52) U.S. Cl. .......................... 435/91.2; 435/6; 435/91.1

(58) Field of Classification Search ........................ None
See application file for complete search history.

(56) References Cited

U.S. PATENT DOCUMENTS

| | | | |
|---|---|---|---|
| 4,683,202 A | 7/1987 | Mullis | |
| 5,268,486 A | 12/1993 | Waggoner et al. | |
| 5,436,149 A | 7/1995 | Barnes | |
| 5,489,523 A | 2/1996 | Mathur | |
| 5,512,462 A | 4/1996 | Cheng | |
| 5,602,011 A | 2/1997 | Luhm et al. | |
| 5,854,033 A | 12/1998 | Lizardi | |
| 5,882,904 A | 3/1999 | Riedl et al. | |
| 2003/0186312 A1 | 10/2003 | Uemori et al. | |

FOREIGN PATENT DOCUMENTS

| WO | WO 01/25483 | 4/2001 |
|---|---|---|
| WO | WO03/056030 | 7/2003 |
| WO | WO 2004111266 A1 * | 12/2004 |

OTHER PUBLICATIONS

Barnes, W. M. (1994). "PCR amplification of up to 35-kb DNA with high fidelity and high yield from λ bacteriophage templates". PNAS, 91(6), 2216-2220.
Bernad, A., Blanco, L., Lázaro, J. M., Martín, G. & Salas, M. (Oct. 6, 1989). "A conserved 3'→5' exonuclease active site in prokaryotic and eukaryotic DNA polymerases". Cell, 59(1), 219-228.
Chakrabarti, R. & Schutt, C. E. (Apr. 2000). "Novel Sulfoxides Facilitate GC-Rich Template Amplification". BioTechniques, 32(4), 866-874.

Cheng, S., Fockler, C., Barnes, W. M. & Higuchi, R. (Jun. 7, 1994). "Effective amplification of long targets from cloned inserts and human genomic DNA". PNAS, 91(12), 5695-5699.
Derbyshire, V., Freemont, P. S., Sanderson, M. R., Beese, L., Friedman, J. M., Joyce, C. M. & Steitz, T. A. (Apr. 8, 1988). "Genetic and crystallographic studies of the 3',5'-exonucleolytic site of DNA polymerase I". Science, 240(4849), 199-201.
Duffaud, G. D., D'Hennezel, O. B., Peek, A. S., Reysenbach, A. & Kelly, R. M. (1998). Systematic Applied Microbiology, 21(1), 40-49.
Frey, M. W., Nossal, N. G., Capson, T. L. & Benkovic, S. J. (Apr. 1, 1993). "Construction and characterization of a bacteriophage T4 DNA polymerase deficient in 3'→5' exonuclease activity". PNAS, 90(7), 2579-2583.
Guo, Z., Guilfoyle, R. A., Thiel, A. J., Wang, R., & Smith, L. M. (1994). "Direct fluorescence analysis of genetic polymorphisms by hybridization with oligonucleotide arrays on glass supports". Nucleic Acids Research, 22(24), 5456-5465.
Herbelin, C. J., Chirillo, S. C., Melnick, K. A. & Whittam, T. S. (Oct. 2000). "Gene Conservation and Loss in the mutS-rpoS Genomic Region of Pathogenic *Escherichia coli*". Journal of Bacteriology, 182(19), 5381-5390.
Lesnik, E. A. & Freier, S. M. (1995). "Relative Thermodynamic Stability of DNA, RNA, and DNA:RNA Hybrid Duplexes: Relationship with Base Composition and Structure". Biochemistry, 34(34), 10807-10815.
Lee, H., Kim, K.-N. & Chae, Y. K. (2007). "Reevaluating the Capability of Taq DNA Polymerase: Long PCR Amplification". Protein & Peptide Letters, 14(4), 321-323.
Pease, A. C., Solas, D., Sullivan, E. J., Cronin, M. T., Holmes, C. P. & Fodor, S. P. (May 24, 1994). "Light-generated oligonucleotide arrays for rapid DNA sequence analysis". PNAS, 91(11), 5027-5029.
Yu, H., Chao, J., Patek, D., Mujumdar, R., Mujumdar, S. & Waggoner, A. S. (1994). "Cyanine dye dUTP analogs for enzymatic labeling of DNA probes". Nucleic Acids Research, 22(15), 3226-3232.
Zakour, N. B., Gautier, M., Andonov, R., Lavenier, D., Cochet, M-F., Veber, P., Sorokin, A., & Le Loir, Y. (2004). "GenoFrag: software to design primers optimized for whole genome scanning by long-range PCR amplification". Nucleic Acids Research, 32(1), 17-24.
Di Giusto, D. A. & King, G. C. (2004). "Strong positional preference in the interaction of LNA oligonucleotides with DNA polymerase and proofreading exonuclease activities: implications for genotyping assays". Nucleic Acids Research, 32(3), e32 (1-8).
Hogrefe, H. & Borns, M. C. (2003). "Amplification: High Fidelity PCR Enzymes". Plainview, NY: Cold Spring Harbor Laboratory Press.

* cited by examiner

*Primary Examiner*—Young J Kim
(74) *Attorney, Agent, or Firm*—Yonggang Ji

(57) ABSTRACT

The present invention provides methods, formulation and kits for the synthesis of long nucleic acid fragments. An improved PCR method is provided for amplifying long DNA fragments. In particular, a single thermostable DNA polymerase is used for the rapid amplification of over 10 kb long DNA fragments. Also provided is a method for extending long complementary DNA strands using this single enzyme formulation.

19 Claims, 14 Drawing Sheets

SINGLE ENZYME SYSTEM FOR FAST, ULTRA LONG PCR

CROSS-REFERENCE TO RELATED APPLICATIONS

This application claims priority to U.S. provisional patent application Nos. 61/016,850 filed Dec. 27, 2007 and 61/025,047 filed Jan. 31, 2008; the entire disclosures of which are incorporated herein by reference in their entireties.

FIELD OF THE INVENTION

The present invention relates to a method for the synthesis of long nucleic acid fragments. In particular, the invention relates to a PCR method for the amplification of long and ultra long nucleic acid fragments using a formulation containing a single DNA polymerase.

BACKGROUND OF THE INVENTION

As the field of Genomics has developed there has been an increasing need to isolate and analyze longer and longer contiguous stretches of nucleic acid. Methods for disease gene discovery and analysis would be facilitated by the ability to easily and rapidly obtain these sequences. For example, the analysis of genetic haplotypes, which require determining marker alleles over long contiguous DNAs, is currently very difficult and frequently done by statistical methods. A method that can simply and rapidly isolate long contiguous stretches of DNA would greatly simplify this analysis and enable new studies in this field.

Current methods for amplifying very long DNAs suffer from several drawbacks. Cheng et al., Proc. Natl. Acad. Sci. USA. 91(12): 5695-5699 (1994). The reactions are slow, with extension times on the order of 1.0 min per kb of extended amplicon. Thus a 20 kb amplicon takes more than 20 min of extension time per cycle or over 6 hours of PCR reaction time. Amplification of larger DNAs is prohibitively slow. Such extended incubations at the elevated temperatures of PCR tax the physical and chemical stability of the nucleotides, DNA and polymerase in the reactions and therefore make improvements difficult. Also the current commercial kit formulations for amplifying DNAs of this length require a mixture of two distinct DNA polymerases, a polymerase with a 3'-5' proofreading activity and a non-proofreading DNA polymerase. Because this formulation requires two polymerases, it is difficult to optimize, troubleshoot or control. Thus, it is desirable to have a method for the rapid amplification of long nucleic acid fragments, using a simple, single enzyme formulation.

A thermostable DNA polymerase gene for Tba DNA polymerase was isolated and cloned from *Thermococcus barossii*, a thermophilic organism obtained from deep vent flange, Endeavor Segment, Juan de Fuca Ridge, off the coast of Washington State in the U.S.A. (Duffaud G D, Syst Appl Microbiol. 21(1):40-49 (1998)). Characterization of the purified Tba DNA polymerase showed that it possesses an active proofreading function in addition to its DNA-dependent DNA polymerase activity. Comparison to other DNA polymerases revealed that Tba DNA polymerase is a member of the Family B DNA polymerases and is approximately 80% conserved compared with the Pfu and *T. littoralis* DNA polymerases (U.S. Pat. No. 5,602,011).

Alteration of the FDIET sequence to FAIAT has been shown in some polymerases to decrease the nuclease activities. (Derbyshire, V. et al., Science 240:199-201, 1988; Bernad, A. et al., Cell 59:219-228, 1989; Frey, M. W. et al., Proc. Natl. Acad. Sci. USA 90:2579-2583, 1993; U.S. Pat. No. 5,489,523) U.S. Pat. No. 5,882,904 discloses that the Tba DNA polymerase can be engineered to have a reduced 3'-5' exonuclease activity. Specifically, the FDIET amino acid sequence (residues 140-144 of native Tba DNA polymerase) has been altered to FAIAT to generated the exo* DNA polymerase.

SUMMARY OF THE INVENTION

A new method for PCR amplification of long DNA fragments is disclosed. This is achieved using a single DNA polymerase system which is also substantially faster than previously known methods particularly for amplification of long sequences greater than about 5 kb. The resulting amplified product may be used as hybridization probes, as sequencing templates and may be digested with restriction endonucleases for fingerprinting or for other downstream analysis purposes.

In one aspect of the invention, a method for PCR amplification of long nucleic acid sequences is provided. The method comprises first providing a nucleic acid target; then adding oligonucleotide primers, a single thermally stable DNA polymerase and deoxynucleoside triphosphates to form a reaction mixture; and then incubating the reaction mixture under thermal cycling conditions to promote amplification of the target by multiple rounds of extension of primers to form amplified PCR product.

The invention improves upon previous PCR methods in that it uses a single DNA polymerase enzyme for amplification of long PCR fragments in the absence of any other enzyme or protein or peptide co-factor. The single enzyme system is capable of amplifying PCR products of at least 10 kb in length, such as at least 20 kb in length, or more than 40 kb in length, or even over 100 kb in length.

The invention further improves upon the previous PCR methods in that the speed of polymerization and thereby amplification is greatly increased. Therefore the extension time required is much less than about one minute per kb, or even less than about one minute per 2 kb, or even less than about one minute per 5 kb. In certain embodiments, the extension time is less than about one minute per 10 kb, or even less than about one minute per 20 kb.

In certain embodiments of the invention, the single thermostable DNA polymerase is one of Tba DNA polymerase, Tba exo* DNA polymerase, Tli DNA polymerase, Tli exo* DNA polymerase, Pfu DNA polymerase, Pfu exo⁻ DNA polymerase, Deep Vent DNA polymerase and Deep Vent exo⁻ DNA polymerase. In a preferred embodiment, the single DNA polymerase is Tba DNA polymerase. In a most preferred embodiment, the single DNA polymerase is Tba exo* DNA polymerase.

In some embodiments, the nucleic acid target being amplified is a low-complexity nucleic acid sample, such as purified DNA from a bacteriophage or virus. In other embodiments, the nucleic acid target being amplified is high-complexity genomic DNA, such as genomic DNA from plants or animals. In a preferred embodiment, the nucleic acid target is human genomic DNA.

In certain embodiments, the amplification primers are exonuclease resistant primers. In one preferred embodiment, the primers have LNA nucleotides or have one or more phosphorothioate linkages in place of the usual phosphodiesters at or near the 3' termini of the primers.

In a second aspect, the invention provides a formulation for PCR amplification of long nucleic acid fragments. The formulation comprises of a single thermostable DNA polymerase, oligonucleotide primers, dNTPs, a nucleic acid template and a reaction buffer suitable for performing the amplification reaction. The PCR product amplified using this formulation is at least 10 kb long, yet the formulation does not include a second enzyme or polymerase or protein or peptide co-factor composition. Preferably, the new formulation amplifies PCR products of at least 20 kb in length, or more than 40 kb in length, or even over 100 kb in length.

An added benefit of the formulation of the invention is that the speed of polymerization or amplification is greatly increased. Therefore the extension time required is less than about one minute for 2 kb, or even one minute for 5 kb. In preferred embodiments, the extension time is less than about one minute for 10 kb or even about one minute for 20 kb.

The single DNA polymerase in the formulation is preferably a Tba DNA polymerase. In a most preferred embodiment, the polymerase is Tba exo* DNA polymerase. The nucleic acid template is either a low complexity nucleic acid sample, such as purified DNA from a bacteriophage or virus, or alternatively high complexity, genomic DNA, such as genomic DNA isolated from plants or animals. In a preferred embodiment, the nucleic acid target is purified human genomic DNA. The amplification primers can include exonuclease resistant primers, such as ones having LNA nucleotides or ones with one or more phosphorothioate linkages in place of the usual phosphodiesters at or near the 3' termini.

In another aspect, the invention provides a kit for PCR amplification of long nucleic acid products of at least 10 kb. The kit comprises a single thermostable DNA polymerase, nucleotides, a reaction buffer suitable for performing the amplification reaction and a user manual. Optionally, the kit also includes oligonucleotide primers that could be exonuclease resistant, containing LNA nucleotides or with one or more phosphorothioate linkages in place of the usual phosphodiesters at or near the 3' termini. The reaction components of the kit are provided in one or more vials. The long PCR kit does not include a second enzyme, polymerase, protein or peptide co-factor composition, yet it amplifies PCR products of at least 20 kb in length, or more than 40 kb in length, or even over 100 kb in length.

An added benefit of the new kit is that the speed of extension is greatly increased. Therefore the extension time required is less than about one minute for 2 kb, or even one minute for 5 kb. In preferred embodiments, the extension time is less than about one minute for 10 kb, or even about one minute for 20 kb.

The single DNA polymerase in the kit is preferably a Tba DNA polymerase. In a most preferred embodiment, the polymerase is Tba exo* DNA polymerase. The kit is suitable for amplifying nucleic acid templates of either a low complexity, or alternatively a high complexity, such as genomic DNA isolated from plants or animals.

In yet another aspect of the invention, a method is provided for synthesizing a complementary strand of a long target nucleic acid molecule. The method comprises first exposing the target nucleic acid molecule to a complementary primer molecule to effect hybridization of the primer to the target; and extending the primer, at high temperature, in the presence of a single thermostable DNA polymerase and dNTPs under polymerization conditions to extend the nucleic acid strand to over 10 kb in length.

The invention uses a single DNA polymerase enzyme for extension of a long, complementary nucleic acid strand in the absence of any other DNA polymerase enzymes. The single enzyme system extends a nucleic acid strand of at least 10 kb in length. Preferably, the new method extends a nucleic acid strand of at least 20 kb in length, or more than 40 kb in length, or even over 100 kb in length. An added benefit of the invention lies in the increased speed of polymerization. The polymerization or extension time required is less than about one minute for 2 kb, or even less than about one minute for 5 kb. In preferred embodiments, the extension time is less than about one minute for 10 kb, or even less than about one minute for 20 kb.

The single thermostable DNA polymerase useful for the complementary strand extension reaction is preferably the Tba DNA polymerase. More preferably, the DNA polymerase is the Tba exo* DNA polymerase. In some embodiments, the nucleic acid target is a low complexity nucleic acid sample. In other embodiments, the target is genomic DNA, such as genomic DNA from plants or animals.

BRIEF DESCRIPTION OF THE DRAWINGS

FIG. 14A. 19-20 kb amplicons. The expected product sizes are indicated. M-DNA marker. FIG. 14B. Tiled approximately 40 kb amplicons. Numbers refer to amplicon map.

DETAILED DESCRIPTION OF THE INVENTION

Figure 1:
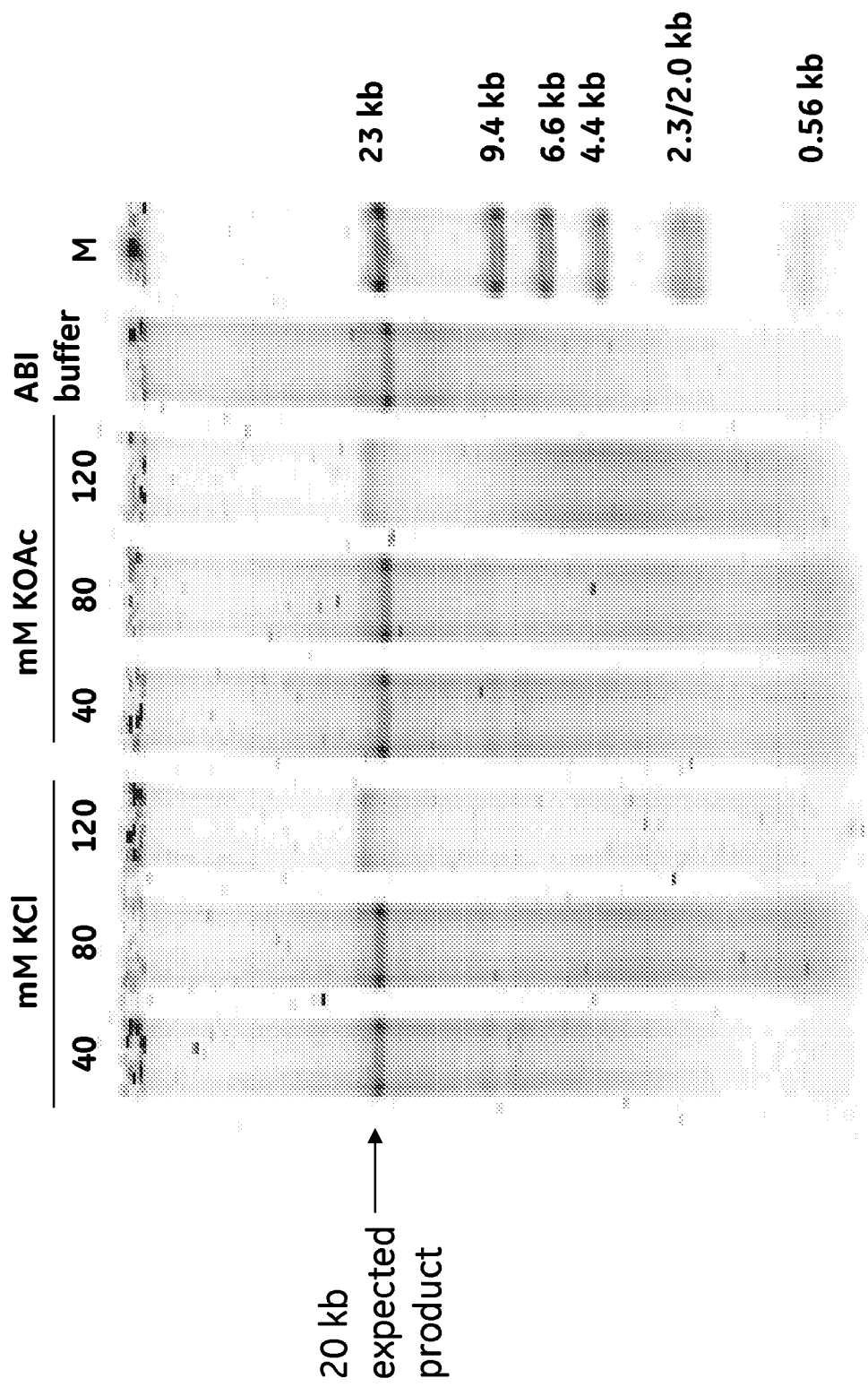
FIG. 1 displays on an agarose electrophoresis gel, the products of an amplification using Tba DNA polymerase to amplify a 20 kb lambda DNA amplicon. The expected product size is indicated. M-DNA markers (Lambda DNA cut with HindIII). Variations in buffer conditions are indicated.

The methods disclosed relate to analysis of DNA and in particular to analyses that depend on the sequence of DNA, often used for determining genotype as well as original sequence information. It also pertains to amplification of DNA sequences. Amplification means synthesis of new strands of DNA that have complimentary sequence to the original, preserving the original sequence information. More specifically, the invention relates to improved methods for the polymerase chain reaction (PCR). Applicants have found that with the improved method, long PCR fragments of greater than 10 kb can be routinely obtained, and at a fraction of the time as compared to previous methods. Also provided are formulations and kits for performing the instant methods.

The polymerase chain reaction (PCR) is defined as a process for amplifying at least one specific nucleic acid sequence contained in a nucleic acid or a mixture of nucleic acids wherein each nucleic acid consists of two separate complementary strands. First, the strands are denatured and combined with two oligonucleotide primers, for the specific sequence being amplified. The primer sequences being chosen such that the extension product synthesized from one primer, when it is separated from its complement, can serve as a template for synthesis initiated by the other primer. The primers are extended using DNA polymerase then the extension products denatured by heating or other means to produce single-stranded molecules. Upon cooling to an annealing temperature, the single-stranded molecules generated anneal with the primers and are again ready to be extended by DNA polymerase at the annealing temperature or extension temperature. The process is repeated one or more times resulting in exponential amplification of the sequences "between" the priming sites (i.e., the amplicon)—see, e.g., U.S. Pat. No. 4,683,202.

Thus one aspect the invention provides a method for PCR amplification of long nucleic acid sequences. The method comprises providing a nucleic acid target; adding oligonucleotide primers, a thermostable DNA polymerase and deoxynucleoside triphosphates (dNTPs) to form a reaction mixture, and incubating the reaction mixture under thermal cycling conditions to promote amplification of the target by extension of primers to form multiple amplified PCR products. Applicants have unexpectedly discovered that, using certain DNA polymerases and buffer compositions, long PCR fragments are routinely amplified. The methods not only amplify long fragments, the extension time required is also reduced substantially. In addition, amplification is achieved using a single thermostable DNA polymerase, without other enzyme, protein or peptide co-factors, an added benefit from the prior art long range PCR amplification methods which require a mixture of two enzymes.

By thermostable is meant having the ability to withstand temperatures up to 95° C. for many minutes without becoming irreversibly inactivated or denatured, and the ability to polymerize DNA at high temperatures (60° to 75° C.). In particular, the inventors have found that certain members of the family B thermostable DNA polymerases are capable, under certain conditions, of amplifying long nucleic acid fragments at an increased speed, in the absence of any additional DNA polymerase enzymes. Preferably, the thermostable DNA polymerase is selected from the group consisting of Tba, *Pyrococcus furiosis* (Pfu), *Thermococcus litoralis* (Tli) and *Pyrococcus* sp. GB-D (Deep Vent) DNA polymerases. Also preferably, the thermostable DNA polymerase has decreased 3'-5' exonuclease activity. The thermostable DNA polymerase is preferably Tba DNA polymerase. Most preferably, the thermostable DNA polymerase is Tba exo* DNA polymerase.

By "Tba DNA polymerase" is meant a DNA polymerase corresponding to one naturally isolated from *Thermococcus barossii*. SEQ ID NO: 1 is an amino acid sequence of one preferred form of Tba DNA polymerase, disclosed in U.S. Pat. No. 5,882,904, the disclosure of which is hereby incorporated by reference in its entirety.

```
Tba DNA polymerase
                                          (SEQ ID NO: 1)
MILDVDYITE DGKPVIRVFK KDKGEFKIEY DREFEPYIYA

LLRDDSAIEE IEKITAERHG KVVKVKRAEK VKKKFLGRSV

EVWVLYFTHP QDVPAIRDKI RKHPAVIDIY EYDIPFAKRY

LIDKGLVPME GDEELKLMSF DIETLYHEGE EFGTGPILMI

SYADESEARV ITWKKIDLPY VDVVSTEKEM IKRFLKVVKE

KDPDVLITYN GDNFDFAYLK KRCEKLGVSF TLGRDGSEPK

IQRMGDRFAV EVKGRIHFDL YPVIRRTINL PTYTLEAVYE

AVFGKPKEKV YAEEIATAWE TGEGLERVAR YSMEDARVTY

ELGREFFPME AQLSRLIGQG LWDVSRSSTG NLVEWFLLRK
```

```
            -continued
AYERNELAPN  KPDERELARR  RGGYAGGYVK  EPERGLWDNI

VYLDFRSLYP  SIIITHNVSP  DTLNREGCKS  YDVAPQVGHK

FCKDFPGFIP  SLLGNLLEER  QKIKRKMKAT  LDPLERKLLD

YRQRAIKILA  NSFYGYYGYA  RARWYCKECA  ESVTAWGREY

IEMVIRELEE  KFGFKVLYAD  TDGLHATIPG  ADAETVKKKA

MEFLNYINPK  LPGLLELEYE  GFYVRGFFVT  KKKYAVIDEE

GKITTRGLEI  VRRDWSEIAK  ETQARVLEAI  LRHGDVEEAV

RIVKEVTEKL  SKYEVPPEKL  VIHEQITREL  KDYKATGPHV

AIAKRLAARG  IKIREGTVIS  YIVLKGSGRI  GDRAIPFDEF

DPTKHRYDAD  YYIENQVLPA  VERILRAFGY  KKEDLRYQKT

RQVGLGAWLG  MGGERLKL
```

By "Tba exo* DNA polymerase" is meant a DNA polymerase engineered to have reduced 3'-5' exonuclease activity, from the naturally isolated Tba DNA polymerase, disclosed in U.S. Pat. No. 5,882,904, the disclosure of which is hereby incorporated by reference in its entirely. SEQ ID NO: 2 shows an amino acid sequence of the Tba exo* DNA polymerase.

```
Tba exo* DNA polymerase
                                      (SEQ ID NO: 2)
MILDVDYITE  DGKPVIRVFK  KDKGEFKIEY  DREFEPYIYA

LLRDDSAIEE  IEKITAERHG  KVVKVKRAEK  VKKKFLGRSV

EVWVLYFTHP  QDVPAIRDKI  RKHPAVIDIY  EYDIPFAKRY

LIDKGLVPME  GDEELKLMSF  AIATLYHEGE  EFGTGPILMI

SYADESEARV  ITWKKIDLPY  VDVVSTEKEM  IKRFLKVVKE

KDPDVLITYN  GDNFDFAYLK  KRCEKLGVSF  TLGRDGSEPK

IQRMGDRFAV  EVKGRIHFDL  YPVIRRTINL  PTYTLEAVYE

AVFGKPKEKV  YAEEIATAWE  TGEGLERVAR  YSMEDARVTY

ELGREFFPME  AQLSRLIGQG  LWDVSRSSTG  NLVEWFLLRK

AYERNELAPN  KPDERELARR  RGGYAGGYVK  EPERGLWDNI

VYLDFRSLYP  SIIITHNVSP  DTLNREGCKS  YDVAPQVGHK

FCKDFPGFIP  SLLGNLLEER  QKIKRKMKAT  LDPLERKLLD

YRQRAIKILA  NSFYGYYGYA  RARWYCKECA  ESVTAWGREY

IEMVIRELEE  KFGFKVLYAD  TDGLHATIPG  ADAETVKKKA

MEFLNYINPK  LPGLLELEYE  GFYVRGFFVT  KKKYAVIDEE

GKITTRGLEI  VRRDWSEIAK  ETQARVLEAI  LRHGDVEEAV

RIVKEVTEKL  SKYEVPPEKL  VIHEQITREL  KDYKATGPHV

AIAKRLAARG  IKIRPGTVIS  YIVLKGSGRI  GDRAIPFDEF

DPTKHRYDAD  YYIENQVLPA  VERILRAFGY  KKEDLRYQKT

RQVGLGAWLG  MGGERLKL
```

The reaction conditions for PCR are well-known in the field of molecular biology. The optimal reaction conditions have been determined for the Tba DNA polymerase (U.S. Pat. No. 5,602,011). For long PCR, the reaction conditions are further optimized. In general, the reactions work reasonably well in a buffer containing Tricine-KOH, pH 8.7, in the presence of a potassium salt and a magnesium salt. In particular, it is found that an increased concentration of dNTPs produces better amplification results. It is also found that between 40-80 mM potassium chloride or potassium acetate is desirable. In addition, a narrow range of magnesium salt concentration is needed for the optimal performance of the reaction system, although the working concentrations depend on the concentration of nucleotides used for each reaction. As with other PCR methods, a suitable detergent is also included in the reaction system for optimal polymerization by the enzyme.

The oligonucleotide primers useful for the current methods are designed to be complementary to certain portions of nucleic acids such that duplexes can be formed between them. The stability of these duplexes can be calculated using known methods such as those described in Lesnick and Freier, Biochemistry 34:10807-10815 (1995). The oligonucleotide primers useful in the processes of amplification can be of any designed length. For example, such primers may be of a length of from at least 10 to about 30-50 nucleotides long, preferably about 10 to 35 nucleotides in length, most preferably from about 15 to about 30 nucleotides in length.

The oligonucleotide primers may be used in single pairs to amplify single regions falling between them. Alternatively multiple single pairs of oligonucleotides, each pair amplifying a single specific region, may be combined in a single reaction to generate a multiplex reaction where multiple specific products are generated in the same reaction. This has the effect of decreasing the number of reactions needed and allows direct comparison of products from the same reaction. As shown in the examples below, the long PCR reactions generated in this system are amenable to multiplexing.

Exonuclease-resistant primers are useful in increasing the yield of amplification reactions. Exonuclease-resistant primers useful in the methods disclosed herein may include modified nucleotides to make them resistant to exonuclease digestion. For example, a primer may possess one, two, three or four phosphorothioate linkages between nucleotides at the 3' end of the primer. Similarly, primers containing locked nucleic acid nucleotides (having 2'-4' methylene-bridged ribose, LNA) can be resistant to exonuclease digestion.

The amplification step can include processes wherein the primers contain at least one nucleotide that makes the primer resistant to degradation, commonly by an enzyme, especially by an exonuclease and most especially by 3'-5'-exonuclease activity. In such an embodiment, at least one nucleotide may be a phosphorothioate nucleotide or some modified nucleotide. Such nucleotide is commonly a 3'-terminal nucleotide but the processes described here also relate to methods where such a nucleotide is located at other than the 3'-terminal position and wherein the 3'-terminal nucleotide of said primer can be removed by 3'-5'-exonuclease activity.

Amplification target DNA useful in the processes disclosed are DNA or RNA molecules, either single or double stranded, including DNA-RNA hybrid molecules generally containing between 10,000 and 500,000 nucleotides. It can be preferable that the DNA is in the range of 10,000 to 200,000 nucleotides. However, it is expected that there will be no upper limit to the size of the target. Where the target is a duplex, such numbers are intended to refer to base pairs rather than individual nucleotide residues. The target templates useful in the processes disclosed herein may have functionally different portions, or segments, making them particularly useful for different purposes. At least two such portions will be complementary to one or more oligonucleotide primers and, when present, are referred to as primer complementary portions or sites. Amplification targets useful in the methods disclosed include, for example, those derived directly from such sources as a bacterial colony, a bacteriophage, a virus plaque, a yeast colony, a baculovirus plaque, as well as native or transiently transfected eukaryotic cells and tissue samples. Such sources may or may not be lysed prior to obtaining the targets. Where such sources have been lysed, such lysis is commonly achieved by a number of means, including where the lysing agent is heat, an enzyme, the latter including, but not limited to, enzymes such as lysozyme, helicase, glucylase, and zymolyase, or such lysing agent may be an organic solvent or a solution of high pH and may include a detergent.

The target nucleic acid may be, for example, a single or double stranded bacteriophage or virus DNA, plasmid, cosmid, BAC, YAC or other construct or vector. Alternatively, the target nucleic acid may be genomic DNA from e.g., bacterium, plant or animal cells or tissue samples. Prior to amplification, the target nucleic acid is optionally purified or enriched.

For certain embodiments of the invention, the target nucleic acids are of low complexity. They are substantially enriched constructs, vectors or nucleic acids from small genomes, i.e., virus and bacteriophage. The target DNA may also be part of a complex mixture, such as crude cellular lysate, or purified genomic DNA. The examples below show that long PCR fragments are successfully amplified using both low complexity sample (e.g., purified bacteriophage lambda DNA) and more complex, genomic DNA sample. In addition the target DNA may vary in GC content, a parameter known to affect the efficiency of amplification. The examples below demonstrate amplification from the extremes of GC content from 35% GC (*Staphylococcus aureus*) to 68% GC (*Rhodobacter spheroides*).

As shown below in the Examples, fragments of 20-47 kb are amplified from purified lambda DNA. Similarly, large fragments of 10 and 22 kb are routinely amplified from bacterial genomic DNA. Our results also suggest that target DNA from more complex genomic DNA samples can be amplified. Human mitochondrial amplicons as well as human genomic fragments were also successfully amplified from human genomic DNA. Therefore, target DNA from a complex starting material can be routinely amplified by our method up to 100 kb in length.

Unexpectedly, the speed of DNA synthesis during the extension phase of the PCR cycle in the current method is also greatly increased as compared to previous PCR methods (~1 kb per minute), including previous long range PCR methods which require a combination of two enzymes. Amplification under the current methods, using a single enzyme, is achieved at a rate of at least 2 kb per minute, and typically at least 5 kb per minute. Target DNA fragments of as long as 22 kb have been synthesized within a minute under the current method.

In some circumstances it may be desirable to quantitatively determine the extent of amplification or DNA yield occurring. In such instances, the amplification step of the present methods work well with any number of standard detection schemes, such as where special deoxynucleoside triphosphates (dNTPs) are utilized that make it easier to perform quantitative measurements. The most common example is where such nucleotide substrates are radiolabeled or have attached thereto some other type of label, such as a fluorescent label or the like. These are typically used in trace amounts so as to minimally disturb the composition of the product DNA. Again, the methods that can be employed in such circumstances are many and the techniques involved are standard and well known to those skilled in the art. Thus, such detection labels include any molecule that can be associated with amplified nucleic acid, directly or indirectly, and which results in a measurable, detectable signal, either directly or indirectly. Many such labels for incorporation into nucleic acids or coupling to nucleic acid probes are known to those of skill in the art. General examples include radioactive isotopes, fluorescent molecules, phosphorescent molecules, enzymes, antibodies, probes, stains, and ligands.

Examples of suitable fluorescent labels include cyanine dyes such as Cy3, Cy3.5, Cy5, and Cy5.5, available from GE Healthcare (U.S. Pat. No. 5,268,486). Further examples of suitable fluorescent labels include fluorescein, 5,6-carboxymethyl fluorescein, Texas red, nitrobenz-2-oxa-1,3-diazol-4-yl (NBD), coumarin, dansyl chloride, and rhodamine. Preferred fluorescent labels are fluorescein (5-carboxyfluorescein-N-hydroxysuccinimide ester) and rhodamine (5,6-tetramethyl rhodamine). These can be obtained from a variety of commercial sources.

Labeled nucleotides are a preferred form of detection label since they can be directly incorporated into the products of amplification during synthesis. Examples of detection labels that can be incorporated into amplified DNA include nucleotide analogs and nucleotides modified with biotin or with suitable haptens such as digoxygenin. Suitable fluorescence-labeled nucleotides are Fluorescein-isothiocyanate-dUTP, Cyanine-3-dUTP and Cyanine-5-dUTP (Yu et al., Nucleic Acids Res., 22:3226-3232 (1994)). A preferred nucleotide analog detection label for DNA is BrdUrd (BUDR triphosphate, Sigma), and a preferred nucleotide analog detection label is Biotin-16-uridine-5'-triphosphate (Biotin-16-dUTP, Boehringher Mannheim). Radiolabels are especially useful for the amplification methods disclosed herein.

Attachment of target templates or oligonucleotide primers to solid supports may be advantageous and can be achieved through means of some molecular species, such as some type of polymer, biological or otherwise, that serves to attach said primer or target template to a solid support. Such solid-state substrates useful in the methods described can include any solid material to which oligonucleotides can be coupled. This includes materials such as polyacrylamide, dextran, agarose, cellulose, nitrocellulose, glass, polystyrene, polyethylene vinyl acetate, polypropylene, polymethacrylate, polyethylene, polyethylene oxide, glass, polysilicates, polycarbonates, TEFLON™, fluorocarbons, nylon, silicon rubber, polyanhydrides, polyglycolic acid, polylactic acid, polyorthoesters, polypropylfumerate, collagen, glycosaminoglycans, and polyamino acids. Solid-state substrates can have any useful form including thin films or membranes, beads, bottles, dishes, fibers, woven fibers, shaped polymers, particles and microparticles. A preferred form for a solid-state substrate is a glass slide or a microtiter dish (for example, the standard 96-well dish). Preferred embodiments utilize glass or plastic as the support. For additional arrangements, see those described in U.S. Pat. No. 5,854,033.

Methods for immobilization of oligonucleotides to solid-state substrates are well established. Oligonucleotides, including address probes and detection probes, can be coupled to substrates using established coupling methods. For example, suitable attachment methods are described by Pease et al., Proc. Natl. Acad. Sci. USA 91(11):5022-5026 (1994). A preferred method of attaching oligonucleotides to solid-state substrates is described by Guo et al., Nucleic Acids Res. 22:5456-5465 (1994).

The long products amplified by the current method are useful for certain applications such as haplotype analysis and sequencing of specific chromosomal loci.

In some methods for rapid PCR amplification of a long nucleic acid fragment, a premix can be used, such as in the form of a kit, comprising a single thermostable DNA polymerase, the four nucleoside triphosphates, an appropriate buffer, and other potentially desirable components, either with each such component in a separate vial or mixed together in different combinations so as to form a total of one, two, three, or more separate vials and, for example, a blank or buffer vial for suspending an intended target nucleic acid for use in the amplification process and a user manual. Optionally, the kit also includes oligonucleotide primers and control templates for a positive control.

One such kit for amplifying DNA sequences comprises a buffer, a single thermostable DNA polymerase and dNTPs. The DNA polymerase can have 3'-5' exonuclease activity. The DNA polymerase can be a Tba DNA polymerase. Alternatively the DNA polymerase can be a Tba exo* DNA polymerase. In some methods, at least one of the normal dNTPs is replaced, in whole or in part, by an analog whose presence in the product DNA confers some advantageous property to the product DNA or to subsequent processes such as sequence-dependent analyses.

Also provided are new formulations for PCR amplification of long nucleic acid fragments of over 10 kb. The formulation includes oligonucleotide primers, dNTP, nucleic acid template, a single thermostable DNA polymerase and a reaction buffer suitable for the amplification reaction. Preferably the single thermostable DNA polymerase is Tba DNA polymerase. Alternatively, the DNA polymerase is Tba exo* DNA polymerase. Optionally, some of the oligonucleotide primers are exonuclease resistant primers such as phosphorothioate modified oligonucleotide primers.

While the methods, kits, formulations and compositions are suitable for the amplification by PCR of long nucleic acid fragments, it is also useful for in vitro synthesis of a complementary strand of a target nucleic acid molecule over a long range (i.e., over 10 kb in length).

Further provided are therefore methods of synthesizing a complementary strand of a long target nucleic acid molecule, comprising the steps of exposing the target nucleic acid molecule to a complementary primer molecule to effect hybridization of the primer to the target, followed by an extension of the primer in the presence of a single DNA polymerase and dNTPs under polymerization conditions. In certain embodiments of the invention, the length of the synthesized strand can be at least 20 kb in length, preferably at least 40 kb in length, more preferably at least 50 kb in length, and most preferably up to 100 kb in length. In these nucleic acid molecule synthesis methods, although there is no exponential amplification of the target as in the PCR methods described above, the primer is, none the less, enlongated extensively. It is noted that for a nucleic acid extension (enlongation) reaction, the buffer and other conditions are substantially similar to that of the long PCR described above. This method is especially suited for the extension of templates with a high GC content.

An additional benefit of the current nucleic acid synthesis methods is in the speed of the reaction. It is shown here that under optimal conditions, the polymerization reaction proceeds at a speed of at least 2 kb per minute, such as at least 5 kb per minute, and preferably at least 10 kb per minute, or even at least 20 kb per minute.

Suitably, the methods of synthesizing a complementary strand of a long target nucleic acid molecule are performed at a high temperature using a thermostable DNA polymerase. Preferably the DNA polymerase is Tba DNA polymerase. Also preferably the DNA polymerase is Tba exo* DNA polymerase.

In carrying out the methods described it is to be understood that reference to particular buffers, media, reagents, cells, culture conditions, pH and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

EXAMPLES

The present examples are provided for illustrative purposes only, and should not be construed as limiting the scope of the present invention as defined by the appended claims. All references given below and elsewhere in the present specification are hereby included herein by reference.

The Following Primers are Used for Certain Examples Below:

For the amplification of Lambda DNA, the primers used are: Forward primer 506: 5'-GCT GAA GTG GTG GAA ACC GC-3' (SEQ ID NO: 3); Reverse primers 23141: 5'-ACA GCC AAG CTT GCA GAA ACG A-3' (SEQ ID NO: 4), 43768: 5'-AAC GTG TCC GCG CCT TTG ATT T-3' (SEQ ID NO: 5), 47513: 5'-TTT CCT GAC AGT GAC AGA CTG CGT-3' (SEQ ID NO: 6), and 21539: 5'-GCC TCG CAT ATC AGG AAG CAC-3' (SEQ ID NO: 7), respectively.

For the amplification of *E. coli* DNA, the primers used are: forward primer fla-FP1: 5'-CGC GCG GTA TTG CTA ACA CG-3' (SEQ ID NO: 8) and reverse primer rpoS-RP1: 5'-GAT TCG CCA GAC GAT TGA AC-3' (SEQ ID NO: 9).

For the amplification of *Staphylococcus aureus* DNA, the primers used are: forward primer A10-F: 5'-TGC CAC TAC CAA CGA TAT GAT CGG T-3' (SEQ ID NO: 10) and reverse primer A10-R: 5'-CCG CTT CAC CTT GAA TTG CTT CTA C-3' (SEQ ID NO: 11). Zakour N. B. et al., Nucleic Acid Research, 32, pp 17-24, 2004.

For the amplification of human mitochondrial DNA, the primers used are: forward primer MK-7F-11673: 5'-CCC CCT GAA GCT TCA CCG G-3' (SEQ ID NO: 12) and reverse primer MT-3R-7608: 5'-CCT ACT TGC GCT GCA TGT GCC-3' (SEQ ID NO: 13).

For certain reactions, phosphorothioate primers are used. These primers are marked with a "–S" after the individual primer name (i.e., 506-S). In these primers, the final and penultimate 3' phosphodiester bonds are phosphorothioates.

Example 1

Amplification of 20-48 kb Amplicons with Tba DNA Polymerase a) Amplification of 20 kb Amplicon from Lambda DNA Amplification was carried out in a final volume of 25 μl using 50 ng of bacteriophage lambda DNA (cI857ind 1 Sam 7) (New England Biolabs) and containing either 25 mM Tricine KOH pH 8.7, 1.4 mM magnesium acetate, 0.02% Rhodafac RE-960 (nonylphenol polyoxyethylene ether, phosphate ester), or GeneAmp XL PCR Kit buffer (Applied Biosystems Inc.), and 0.2 mM dATP, 0.2 mM dCTP, 0.2 mM dTTP, 0.2 mM dGTP, 0.4 μM of forward primer 506, 0.4 μM reverse primer 21539. Amounts of KCl or potassium acetate were varied as indicated in FIG. 1. Reactions were assembled on ice followed by addition of 15 ng of Tba DNA polymerase and initiated by placing in the PCR thermal cycler preheated to 94° C.

Cycling was as Follows:

Stage 1—94° C.—1 min

Stage 2—15 repeats
94° C.—15 sec
68° C.—30 sec
72° C.—2.5 min

Stage 3—72° C. 10 min
4° C. to storage

Samples were recovered and 0.5 μl of reaction was mixed with 5 μl 1×TAE buffer (1×=40 mM Tris-Acetate pH 7.9, 5 mM Sodium Acetate, 0.3 mM EDTA)+0.1% w/v SDS and heated at 65° C. for 2 min. The products along with DNA size markers were separated by gel electrophoresis on 0.3% SEAKEM GOLD™ Agarose Gels (Cambrex) in 1×TAE. Agarose Gels were then stained by GELSTAR™ (Cambrex) per manufacturer's instructions and products were visualized on a TYPHOON™ 8600 scanner (GE Healthcare) for analysis.

We have examined the ability of Tba DNA polymerase to synthesize amplicons of 20 kb under several conditions and types of salt. There is good yield of 20 kb amplicons with 40-80 mM salt (KCl or potassium acetate) in these reactions with decreasing yield at higher salt. The yields from this simplified buffer system are equivalent to use of a buffer system obtained from Applied Biosystems Inc. (FIG. 1).

b) Amplification of 47 kb Amplicon from Lambda DNA

Amplification was carried out in a final volume of 25 μl using 50 ng of bacteriophage lambda DNA (cI857ind 1 Sam 7) and containing 25 mM Tricine KOH pH 8.7, 40 mM potassium acetate 2.6 mM magnesium acetate, 0.02% RE-960, 0.5 mM dATP, 0.5 mM dCTP, 0.5 mM dTTP, 0.5 mM dGTP, 0.4 μM of forward primer 506-S, 0.4 μM reverse primer 47513-S and indicated amounts of ET-SSB. Reactions were assembled on ice followed by addition of 15 ng Tba or 20 ng Tba Exo* DNA polymerase and initiated by placing in the PCR thermocycler preheated to 94° C.

Cycling was as Follows:

Stage 1—94° C.—1 min

Stage 2—15 repeats
94° C.—15 sec
68° C.—30 sec
69° C.—10 min

Stage 3—72° C. 10 min
4° C. to storage

Samples were recovered and analyzed as in Example 1a.

Figure 2:
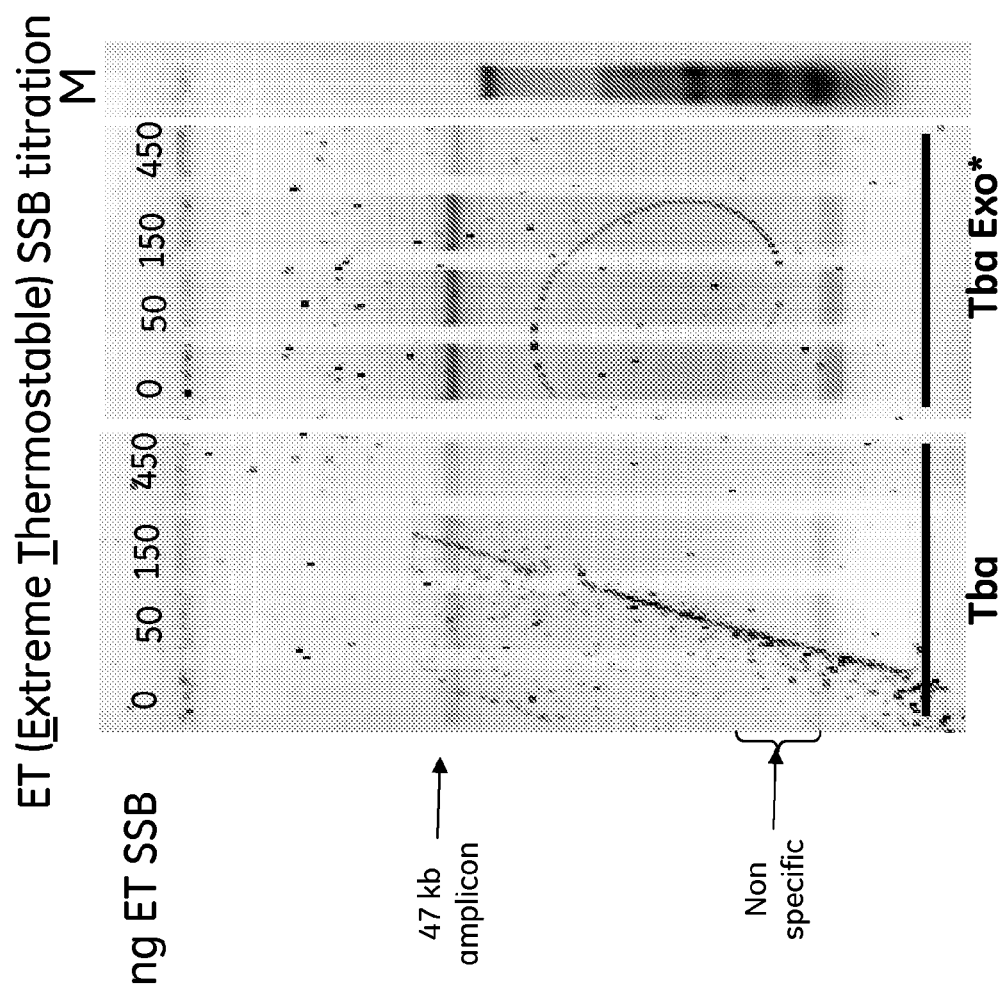
FIG. 2 displays on an agarose electrophoresis gel, the products of an amplification using Tba or Tba Exo* DNA polymerase to amplify a 47 kb lambda DNA amplicon with varying amounts of a thermostable single stranded DNA binding protein from New England Biolabs (ET SSB). The expected product size is indicated. M-DNA markers.

To extend the amplicon length, both Tba and Tba Exo* DNA polymerase were allowed to amplify a 47 kb amplicon comprising 98% of the lambda DNA template. Both enzymes gave robust amplification of the expected product with the Exo* enzyme having better yield. There have been literature reports that single-stranded DNA binding proteins (SSBs) can improve the yields and specificities of PCR reactions. Addition of a commercially available thermostable SSB (ET-SSB) did not enhance these PCR reactions with inhibition seen at very high amounts of added LT-SSB (FIG. 2). We conclude that our single enzyme system is able to amplify the longest linear DNA we have tested at 47 kb. Further experiments examined the relative effects of changing the reaction parameters to improve reaction yield.

c) Effect of Extension Time on the Amplification

Amplification was carried out in a final volume of 25 μl using 50 ng of bacteriophage lambda DNA (cI857ind 1 Sam 7) and containing either 25 mM Tricine KOH pH 8.7, 40 mM potassium acetate, 1.4 mM magnesium acetate, 0.02% RE-960, or GeneAmp XL PCR Kit buffer (Applied Biosystems Inc.), and 0.2 mM dATP, 0.2 mM dCTP, 0.2 mM dTTP, 0.2 mM dGTP, 0.4 μl of forward primer 506-S, 0.4 μl reverse primer 21539-S. Reactions were assembled on ice followed by addition of 20 ng of Tba DNA polymerase and initiated by placing in the PCR thermocycler preheated to 94° C.

Cycling was as Follows:

Stage 1—94° C.—1 min

Figure 3:
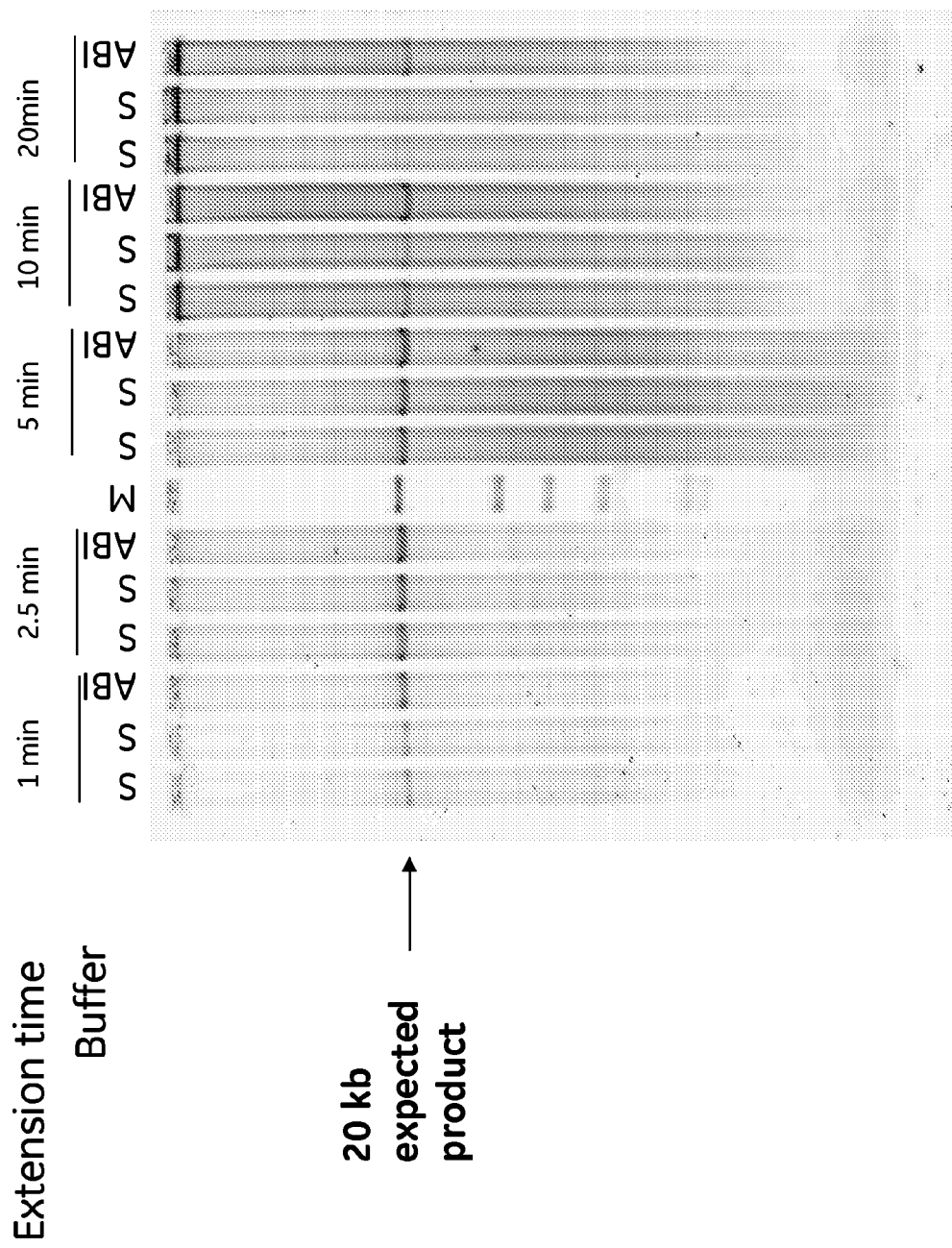
FIG. 3 displays on an agarose electrophoresis gel, the products of an amplification using Tba DNA polymerase to amplify a 22 kb lambda DNA amplicon. The expected product size is indicated. M-DNA marker. Variations in buffer conditions are indicated: S-standard buffer, ABI-GeneAmp XL PCR buffer. Extension times are indicated.

Stage 2—15 repeats
94° C.—15 seq
68° C.—30 seq
72° C.—Indicated extension time (see FIG. 3)

Stage 3—72° C. 10 min
4° C. to storage

Samples were recovered and analyzed as in Example 1a.

The effect of extension time on long PCR was examined on 20 kb amplicons from lambda DNA in several buffer systems. Good yield of product was obtained in as little as one minute of extension time indicating an extension rate of over 300 nucleotides/sec with slight variations in the yield among the buffers tested. Increasing the extension time resulted in increasing the amount of product, however longer times (10-20 min.) resulted in the accumulation of large molecular weight non-specific material seen in the wells of the gel (FIG. 3). The optimum conditions for amplification are approximately 2.5-5 minutes for the 20 kb amplicon or a rate of 0.1-0.2 min/kb, a time much shorter than previously demonstrated methods.

d) Variation of dNTP Concentration and Extension Temperature Increases Yield of PCR Product Amplification was carried out using either 5 or 50 ng of bacteriophage lambda DNA (cI857ind 1 Sam 7) in a final volume of 25 μl containing 25 mM Tricine KOH pH 8.7, 40 mM potassium acetate, 1.4 mM magnesium acetate, 0.02% RE-960, and 0.4 μM of forward primer 506-S, 0.4 μM reverse primer 23141-S. dNTPs were varied by the given amounts with all four nucleotides having the same given concentration in each reaction. Magnesium concentration was adjusted to be 0.6 mM greater than the total dNTP concentration throughout. Reactions were assembled on ice followed by addition of 15 ng Tba or 20 ng Tba Exo* DNA polymerase and initiated by placing in the PCR thermocycler preheated to 94° C.

Cycling was as Follows:

Stage 1—94° C.—1 min

Stage 2—15 repeats
94° C.—15 sec
68° C.—30 sec
69° C. or 72° C.—4 min

Stage 3—72° C. 10 min
4° C. to storage

Samples were recovered and analyzed as in Example 1a.

Figure 4:
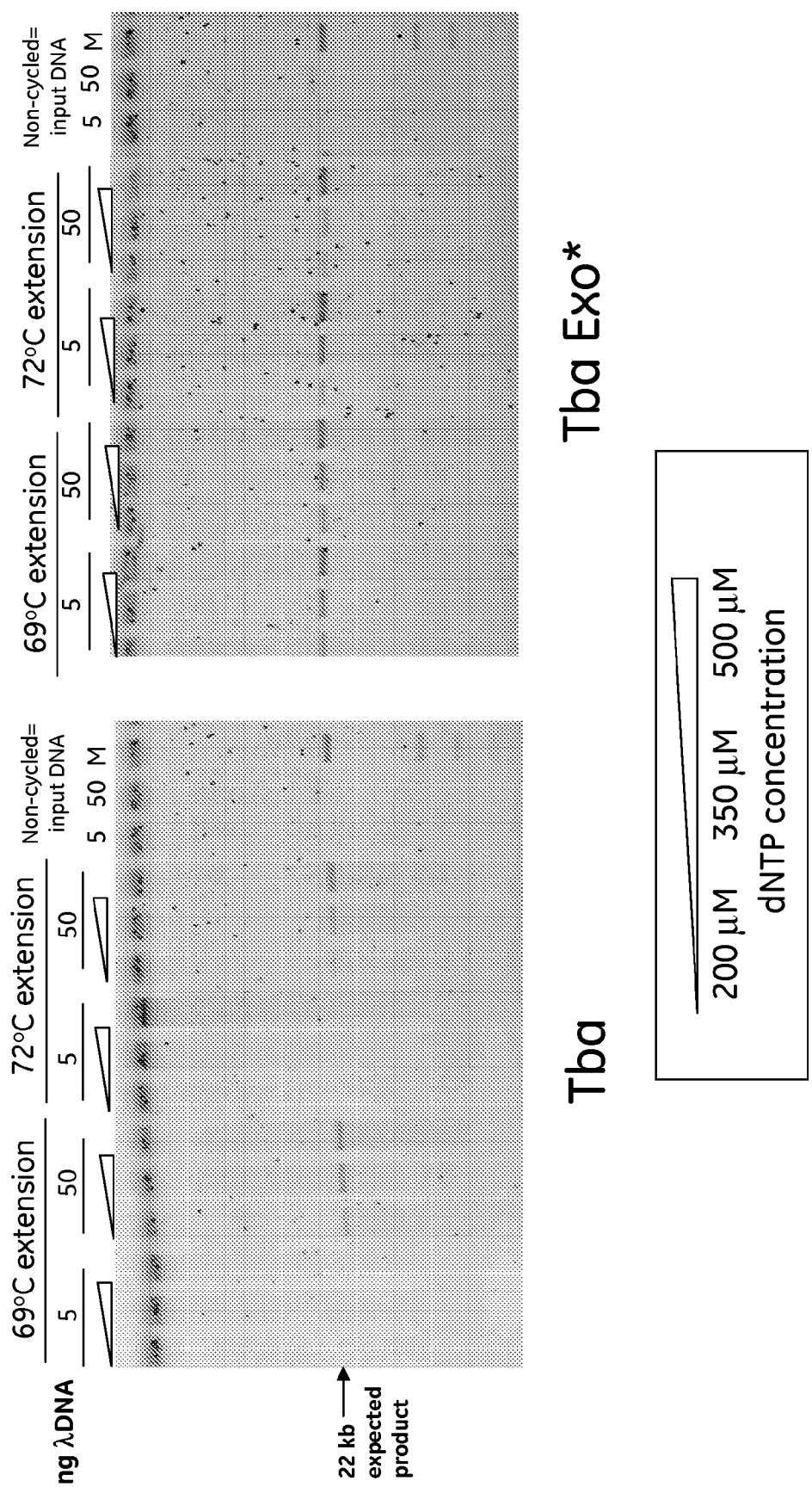
FIG. 4 displays on an agarose electrophoresis gel, the products of an amplification using Tba or Tba Exo* DNA polymerase to amplify a 22 kb lambda DNA amplicon. The expected product size is indicated. M-DNA marker. Variations in extension temperature and nucleotide concentrations and template DNA amounts are indicated. The last set of lanes contains equivalent volumes of starting reactions without PCR cycling.

Here, we increased the concentration of all four dNTPs while maintaining a constant excess of magnesium to help drive the polymerization reaction. Increasing dNTPs concentrations resulted in better yields of 22 kb product DNA in all cases (compare first and third lanes in each set of three). In addition we examined the effect of extension temperature for this reaction as well as the relative sensitivity of the two variants of Tba DNA polymerase. The slight decrease in temperature of the extension reaction from 72° C. to 69° C. had a marginal to slightly positive effect. More interestingly, the Tba Exo* DNA polymerase showed much higher activity at the lower concentration of template (FIG. 4).

e) Titration of Magnesium

Amplification was carried out using 50 pg of bacteriophage lambda DNA (cI857ind 1 Sam 7) in a final volume of 25 µl containing 25 mM Tricine KOH pH 8.7, 40 mM potassium acetate, 0.02% RE-960, and 0.5 mM dATP, 0.5 mM dCTP, 0.5 mM dTTP, 0.5 mM dGTP, 0.4 µM of forward primer 506-S, 0.4 µM reverse primer 23141-S. Total magnesium concentration is indicated. Reactions were assembled on ice followed by addition of 20 ng Tba Exo* DNA polymerase and initiated by placing in the PCR thermocycler preheated to 94° C.

Cycling was as Follows:

Stage 1—94° C.—1 min

Stage 2—15 repeats
   94° C.—15 sec
   68° C.—30 sec
   69° C.—4 min

Stage 3—72° C. 10 min
   4° C. to storage

Samples were recovered and analyzed as in Example 1a.

Figure 5:
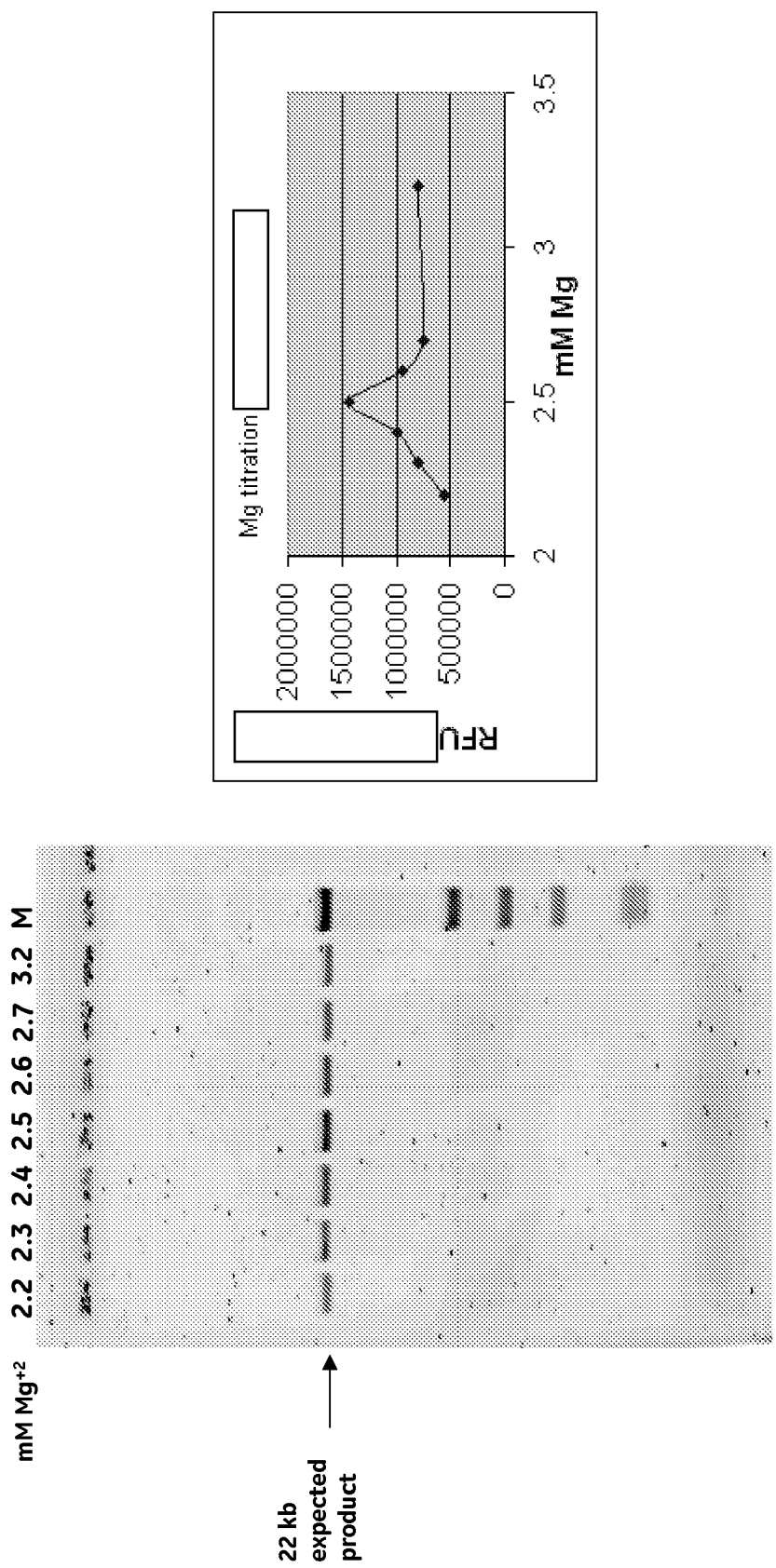
FIG. 5 displays on an agarose electrophoresis gel, the products of an amplification using Tba Exo* DNA polymerase to amplify a 22 kb lambda DNA amplicon with varying concentrations of magnesium acetate. The expected product size is indicated. M-DNA marker. Also presented is a quantitative graph of band intensity.

Long PCR reactions are known to be very sensitive to concentration of magnesium salts. To assess whether our chosen conditions are optimal, we performed a reaction with high sensitivity (50 pg input DNA) and varied the magnesium concentration. Although the correct product size was made in all cases, there is a sharp optimum in concentration of magnesium at 2.4 mM-2.6 mM added magnesium acetate (FIG. 5). This is within the range of our experiments and indicates that tight control over the concentration of magnesium divalent cation is required in this system.

Example 2

High Sensitivity of Amplification with Tba DNA Polymerases

Amplification was carried out in a final volume of 25 µl using indicated amounts of bacteriophage lambda DNA (cI857ind 1 Sam 7) and containing 25 mM Tricine KOH pH 8.7, 40 mM potassium acetate, 2.6 mM magnesium acetate, 0.02% RE-960, 0.5 mM dATP, 0.5 mM dCTP, 0.5 mM dTTP, 0.5 mM dGTP, 0.4 µM of forward primer 506-S, 0.4 µM reverse primer 23141-S. Reactions were assembled on ice followed by addition of 15 ng Tba or 20 ng Tba Exo* DNA polymerase and initiated by placing in the PCR thermocycler preheated to 94° C.

Cycling was as Follows:

Stage 1—94° C.—1 min

Stage 2—15 repeats
   94° C.—15 sec
   68° C.—30 sec
   69° C.—4 min

Stage 3—72° C. 10 min
   4° C. to storage

Samples were recovered and analyzed as in Example 1a.

Figure 6:
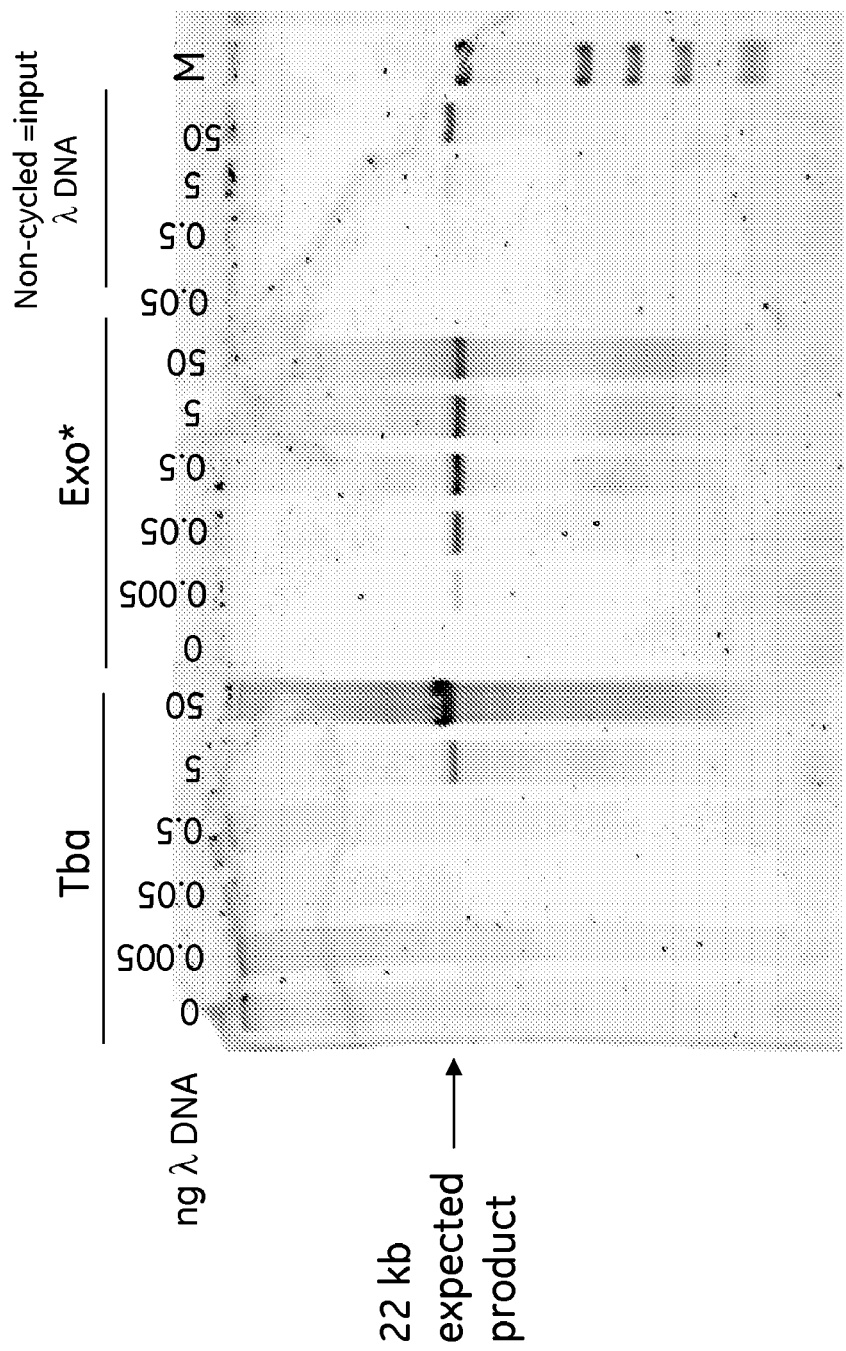
FIG. 6 displays the products of an amplification using Tba or Tba Exo* DNA polymerase to amplify a 22 kb lambda DNA amplicon with varying concentrations of input template DNA. The expected product size is indicated. M-DNA marker. The last set of lanes contains equivalent volumes of starting reactions without PCR cycling.

Given the observation above that the Tba Exo* polymerase was able to use lower amounts of input template, the relative sensitivity of the two forms of Tba DNA polymerase was evaluated. Decreasing amounts of template were added to the amplification reaction. Wild type Tba DNA polymerase was able to synthesize 22 kb amplicons only at relatively high concentrations (>5 ng) of template under these conditions. Amplification with the Exo* form however had at least 1000 fold higher sensitivity. A high yield of 22 kb product was synthesized from as little as 50 pg of starting lambda DNA with measurable product with 5 pg input DNA (FIG. 6). This represents a high degree of amplification over input starting DNA. This represents a much higher level of sensitivity for synthesis of these very long product DNAs than previously reported and is very useful for analysis of long amplicons in genomic DNAs.

Example 3

Amplification in the Presence of High Concentrations of Human DNA

Figure 7:
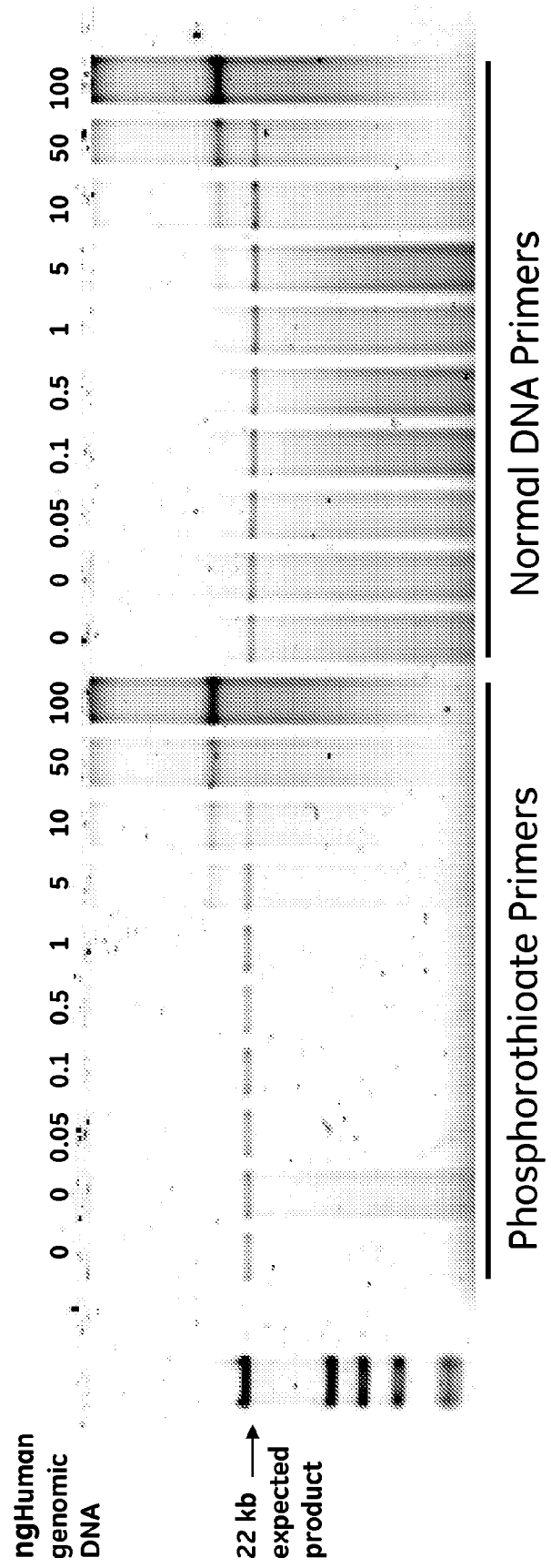
FIG. 7 displays on an agarose electrophoresis gel, the products of an amplification using Tba Exo* DNA polymerase to amplify a 22 kb lambda DNA amplicon in the presence of increasing amounts of human genomic DNA with either normal or phosphorothioate primers. The expected product size is indicated. M-DNA marker.

Amplification was carried out in a final volume of 25 µl using 5 pg of bacteriophage lambda DNA (cI857ind 1 Sam 7) and containing 25 mM Tricine KOH pH 8.7, 40 mM potassium acetate, 2.4 mM magnesium acetate, 0.02% RE-960, 0.5 mM dATP, 0.5 mM dCTP, 0.5 mM dTTP, 0.5 mM dGTP, 0.4 µM of forward primer 506, 0.4 µM reverse primer 23141 (either normal or phosphorothioate-containing as indicated in FIG. 7). Amounts of Human Jurkat (T-cell leukemia) Genomic DNA (New England Biolabs) were varied as indicated. Reactions were assembled on ice followed by addition of 40 ng of Tba Exo* DNA polymerase and initiated by placing in the PCR thermocycler preheated to 94° C.

Cycling was as Follows:

Stage 1—94° C.—1 min

Stage 2—15 repeats
   94° C.—15 sec
   68° C.—30 sec
   69° C.—2.5 min

Stage 3—69° C. 10 min
   4° C. to storage

Samples were recovered and analyzed as in Example 1a.

For these enzymes to be useful in the amplification of genomic DNAs, they must not be affected to a great extent by the presence of a large excess of non-specific sequences that would be present when performing PCR on a specific genomic DNA. The activity of Tba Exo* using very low target concentrations was tested for sensitivity to contaminating genomic DNA. Amplification of 5 pg of lambda template to a 22 kb amplicon was not effected by up to $10^4$ excess (by mass) genomic DNA (FIG. 7). This relative insensitivity to non-specific genomic DNA allowed for the testing of long PCR from sequences embedded in genomic DNA itself.

Example 4

Amplification of Bacteria Genomic DNA a) Amplification of 10.9 kb amplicon from E. coli Genomic DNA E. coli genomic DNA was isolated using the ILLUSTRA™ Bacterial genomic DNA mini-spin Kit (GE Healthcare) according to manufacturer's instructions. Amplification was carried out in a final volume of 25 µl using indicated amount of DNA in 25 mM Tricine KOH pH 8.7, 40 mM potassium acetate, 2.4 mM magnesium acetate, 0.02% polyoxyethylene nonylphenol ether phosphate methyl ester (Rhodafac RE-960 Rhone Poulenc), 0.5 mM dATP, 0.5 mM dCTP, 0.5 mM dTTP, 0.5 mM dGTP, 0.4 µM of forward primer fh1A-FP1-S, 0.4 µM reverse primer rpoS-RP1-S (J. Bact. (2000) 182 pp 5381-5390). Reactions were assembled on ice followed by addition of 40 ng of Tba Exo* DNA polymerase and initiated by placing in the PCR thermocycler preheated to 94° C.

Cycling was as Follows:

Stage 1—94° C.—1 min

Stage 2—15 repeats
94° C.—15 sec
68° C.—30 sec
69° C.—either 1 or 2.5 min

Stage 3—69° C. 10 min
4° C. to storage

Samples were recovered and analyzed as in Example 1a.

Figure 8:
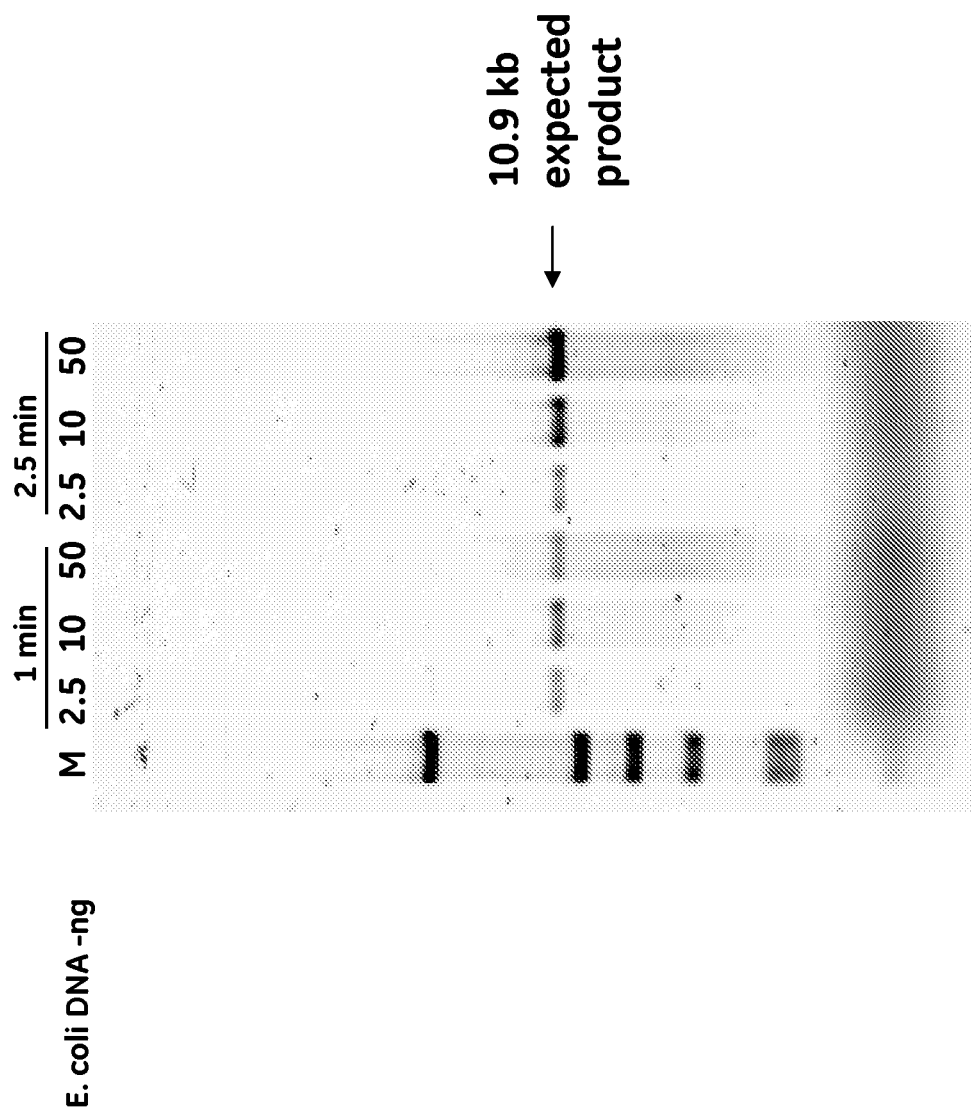
FIG. 8 displays on an agarose electrophoresis gel, the products of an amplification using Tba Exo* DNA polymerase to amplify a 10.9 kb *E. coli* genomic DNA amplicon. Amounts of *E. coli* genomic DNA are indicated, as are variations in PCR extension times. The expected product size is indicated. M-DNA marker.

A specific 10.9 kb amplicon was easily and cleanly amplified out of purified E. coli DNA yielding the expected size product in all conditions tested. Although we can see product with as little as one minute extension times, the yield improves when the extension time increases. Increasing the amount of starting material improves yield (compare 2.5 ng to 10 ng input DNA) but further increases in input template have no effect suggesting the system is saturated for template at this point (FIG. 8). By way of comparison, the original amplification of these primer sets (J. Bact. (2000) 182 pp 5381-5390) took greater than 12 hours while the amplification described was run in under 1.5 hours further demonstrating the utility of this enzyme system.

b) Amplification of 22 kb Lambda Lysogen Amplicon from E. coli Genomic DNA

E. coli genomic DNA was isolated from a strain containing a lambda lysogen (JS4588 lambda+) using the ILLUSTRA™ Bacterial genomic DNA mini-spin Kit according to manufacturer's instructions. Amplification was carried out in a final volume of 25 µl using indicated amount of DNA in 20 mM Tricine KOH pH 8.7, 40 mM potassium acetate, 2.4 mM magnesium acetate, 0.02% RE-960, 0.5 mM dATP, 0.5 mM dCTP, 0.5 mM dTTP, 0.5 mM dGTP, 0.4 µM of forward primer 506, 0.4 µM reverse primer 23141. Reactions were assembled on ice followed by addition of 40 ng of Tba Exo* DNA polymerase and initiated by placing in the PCR thermocycler preheated to 94° C.

Cycling was as Follows:

Stage 1—94° C.—1 min

Stage 2—15 repeats
94° C.—15 sec
68° C.—30 sec
69° C.—either 2.5 or 5 min

Stage 3—69° C. 10 min
4° C. to storage

Samples were recovered and analyzed as in Example 1a.

Figure 9:
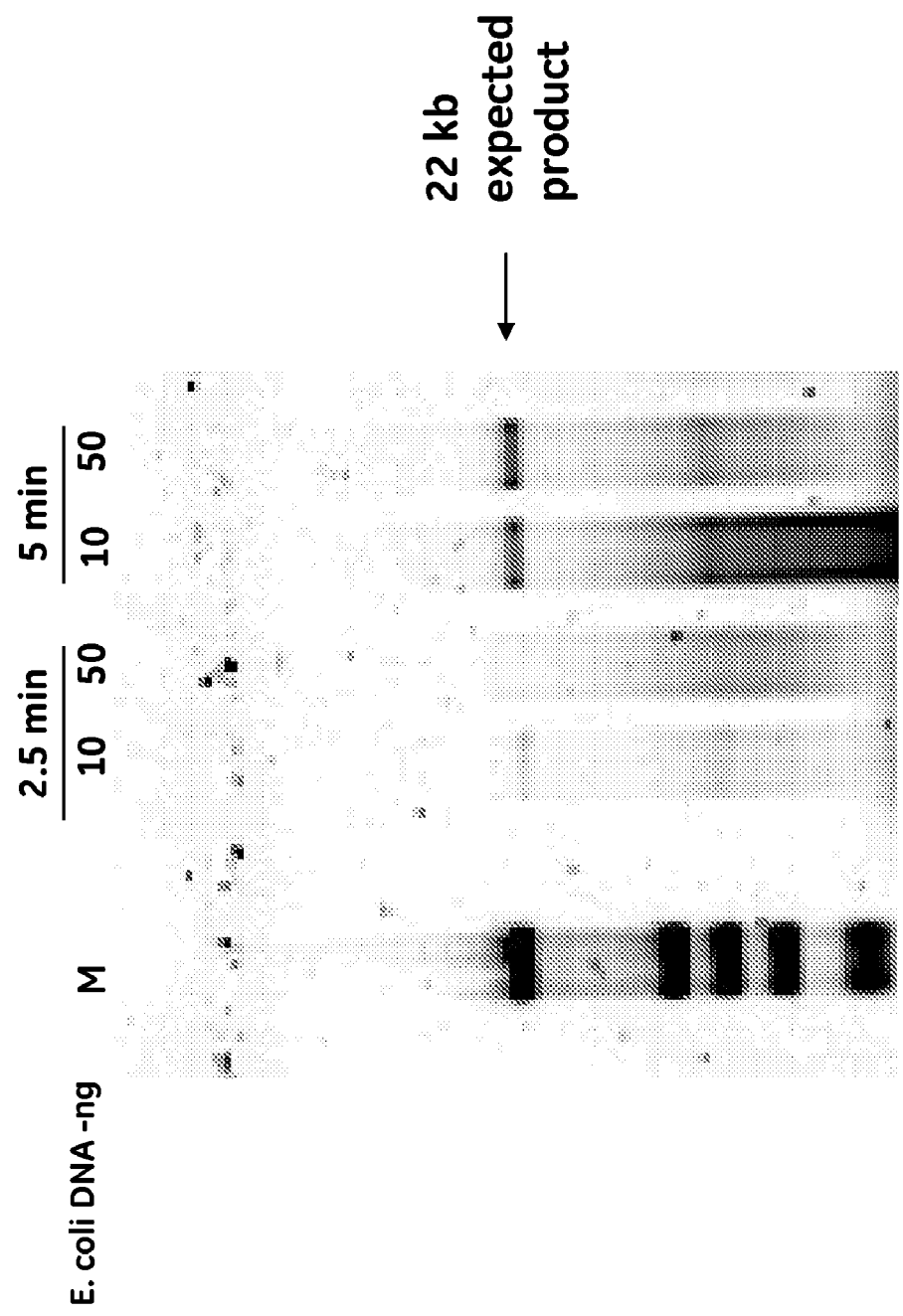
FIG. 9 displays on an agarose electrophoresis gel, the products of an amplification using Tba Exo* DNA polymerase to amplify a 22 kb lambda lysogen amplicon in *E. coli* genomic DNA. Amounts of *E. coli* genomic DNA are indicated, as are variations in PCR extension times. The expected product size is indicated. M-DNA marker.

To further extend the lengths of genomic DNA amplified, DNA from a lambda lysogen was prepared. Amplification of this lambda DNA embedded in the context of E. coli genomic DNA was examined allowing direct comparison to the examples above with purified lambda DNA. Amplification of the 22 kb lambda DNA amplicon resulted in the correct size product in good yield (FIG. 9). The amplification time in this context is somewhat longer than for purified DNAs, however is still rapid relative to previous methods and demonstrates the utility of this method for amplifying long stretches of genomic DNA.

c) Amplification of 10.9 kb Genomic DNA Amplicon from Staphylococcus aureus

Genomic DNA from three strains of Staphylococcus aureus subsp. aureus was obtained from ATCC (Staphylococcus aureus subsp. aureus ATTC® 10832D-5™, Staphylococcus aureus subsp. aureus ATTC® 35556™=SA113, and Staphylococcus aureus subsp. aureus ATTC® 700699™). Amplifications were carried out in a final volume of 25 µl using indicated amount of DNA in Tricine KOH pH 8.7, 40 mM potassium acetate, 2.4 mM magnesium acetate, 0.02% polyoxyethylene nonylphenol ether phosphate methyl ester (Rhodafac RE-960 Rhone Poulenc), 0.5 mM dATP, 0.5 mM dCTP, 0.5 mM dTTP, 0.5 mM dGTP, 0.4 µM of forward primer A10-F, 0.4 µM reverse primer A10-R (Zakour, B. N. et al., Nuc. Acids Research 32:17-24 (2004)). Reactions were assembled on ice followed by addition of 40 ng of Tba Exo* DNA polymerase and initiated by placing in the PCR thermocycler preheated to 94° C.

Cycling was as Follows:

Stage 1—94° C.—1 min

Stage 2—15 repeats
94° C.—15 sec
68° C.—30 sec
69° C.—either 1 or 2.5 min, as indicated Stage 3—69° C. 10 min
4° C. to storage Samples were recovered and analyzed as in Example 1a.

Figure 10:
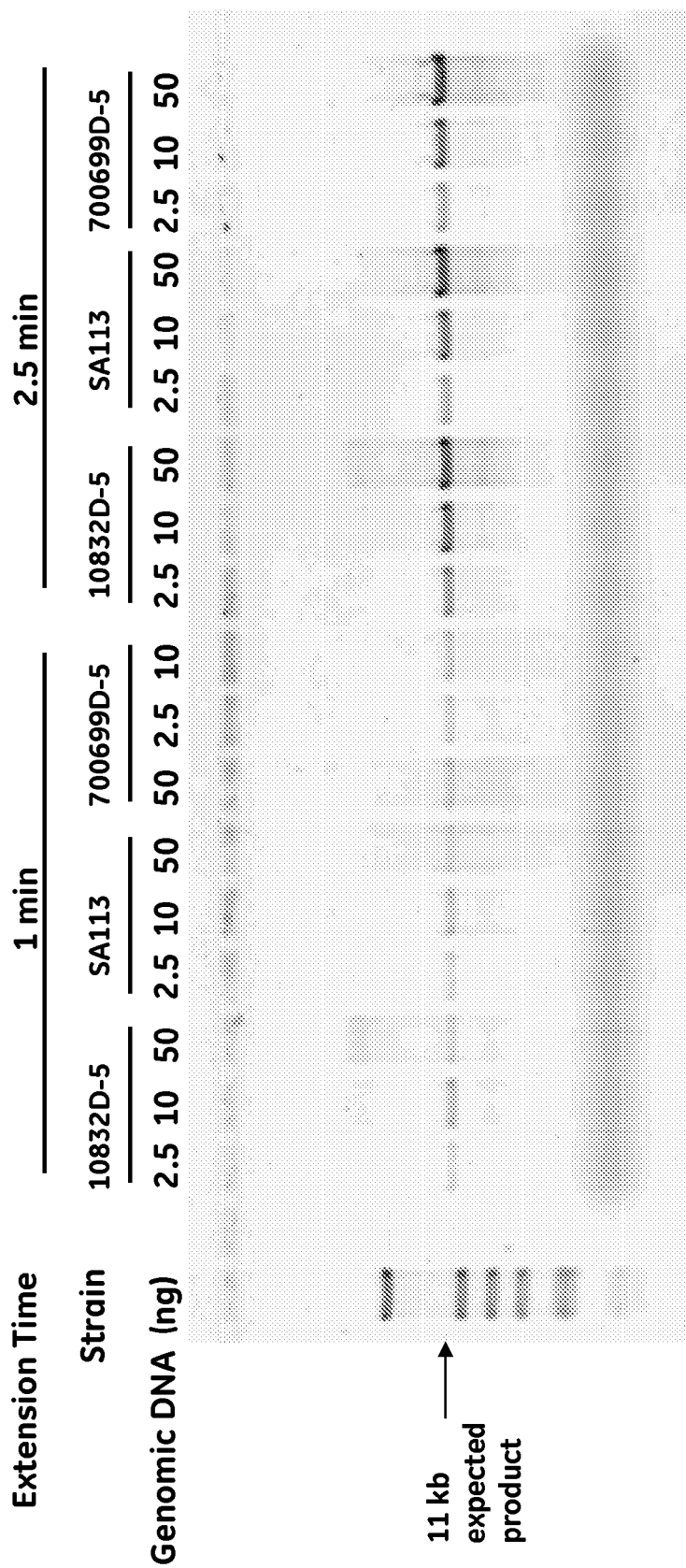
FIG. 10 displays on an agarose electrophoresis gel, the products of an amplification using Tba Exo* DNA polymerase to amplify a 10.9 kb amplicon from genomic DNA isolated from three strains of *Staphylococcus aureus* subsp. *aureus*. Amounts of *S. aureus* genomic DNA are indicated, as are variations in PCR extension times. The expected product size is indicated.

A specific 10.9 kb amplicon was easily and cleanly amplified out of purified Staphylococcus aureus subsp. aureus DNA yielding the expected size product in all conditions tested. Although product is amplified with as little as one minute extension time, the yield improves when the extension time increases. Increasing the amount of starting material improves yield (compare 2.5 ng to 10 ng input DNA) but further increases in input template have no effect suggesting the system is saturated for template at this point (FIG. 10). By way of comparison, the original amplification of this primer set (Zakour, B. N. et al., Nuc. Acids Research 32:17-24 (2004)) took greater than 8 hours while the amplification described here was run in under 1.5 hours further demonstrating the utility of this single enzyme system.

d) Amplification of Amplicons from Rhodobacter spheroides

Genomic DNA from Rhodobacter sphaeroides was obtained from ATCC® (Rhodobacter sphaeroides (van Niel) Imhoff et al. ATTC® BAA-808™). Amplifications were carried out in a final volume of 25 µl using 10 ng of genomic DNA in Tricine KOH pH 8.7, 40 mM potassium acetate, 2.5 mM magnesium acetate, 0.02% polyoxyethylene nonylphenol ether phosphate methyl ester (Rhodafac RE-960 Rhone-Poulenc), 0.5 mM dATP, 0.5 mM dCTP, 0.5 mM dTTP, 0.5 mM dGTP, 0.1 µM of forward primer, 0.1 µM reverse primer and indicated amounts of tetramethylene sulphoxide (TMSO). Reactions were assembled on ice followed by addition of 100 ng of Tba Exo* DNA polymerase and initiated by placing in the PCR thermocycler preheated to 98° C.

Figure 11:
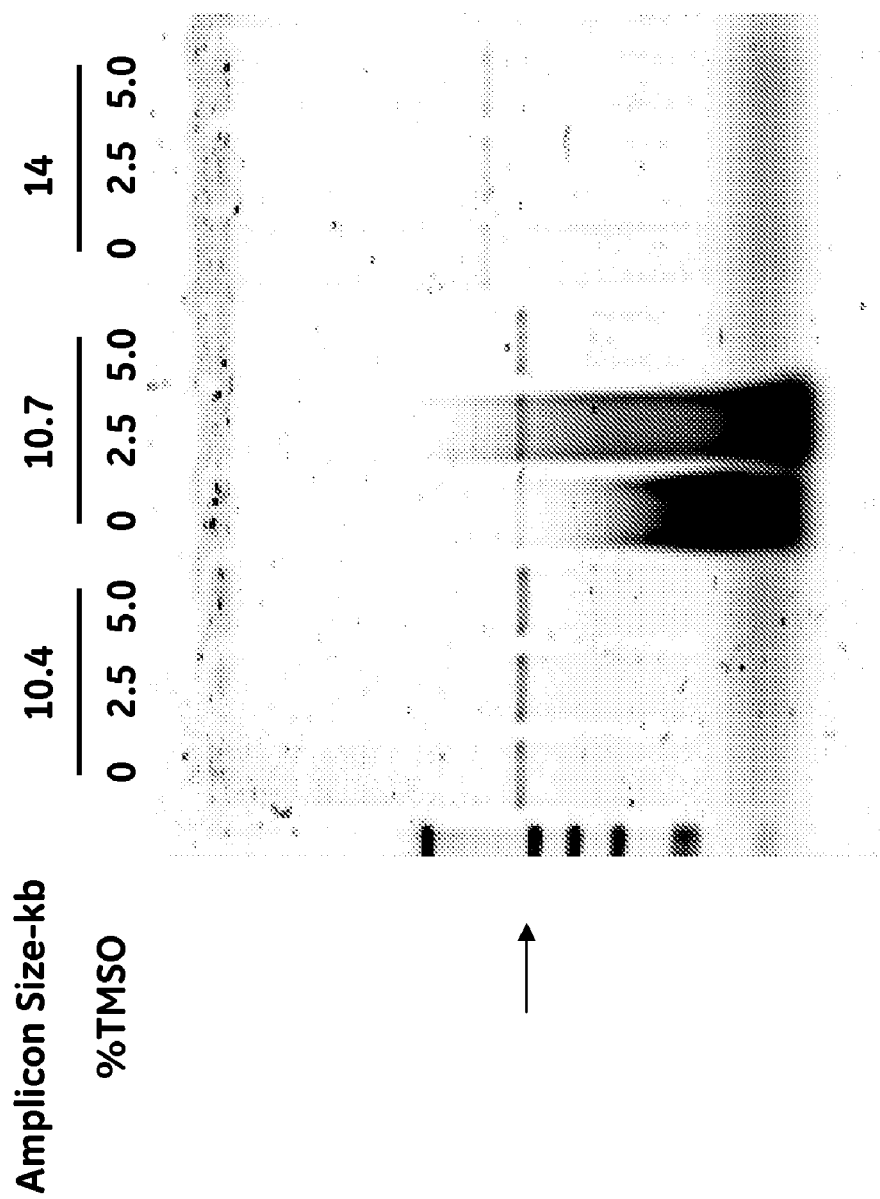
FIG. 11 displays on an agarose electrophoresis gel, the products of an amplification in the presence of various concentrations of tetramethylene sulfoxide (TMSO) using Tba Exo* DNA polymerase of several amplicons from 10 ng of the very GC rich genomic DNA isolated from *Rhodobacter spheroides*. The expected product sizes are given.

The primers used were named after the expected amplification product size, shown on FIG. 11. The primers are: Rs 10.4 forward: 5'-CCA GCG GCG GGG TCA GGT GCG TTA C-3' (SEQ ID NO: 14) and Rs 10.4 reverse: 5'-GAG CCG GCG AAG GTC CAG GAA TGT TTG-3' (SEQ ID NO: 15); Rs 10.7 forward: 5'-GGT GCT GCC GGT GAT CGA GGA GTT GA-3' (SEQ ID NO: 16) and Rs 10.7 reverse: 5'-CGC CGC AGA CGC ACC CGA GGA GAC AC-3' (SEQ ID NO: 17); and Rs 14 forward: 5'-CCA GCG GCG GGG TCA GGT GCG TTA C-3' (SEQ ID NO: 18) and Rs 14 reverse: 5'-CCA GAG GCC GGG CGT GTG ATA CTT-3' (SEQ ID NO: 19).

Cycling was as Follows:

Stage 1—98° C.—1 min

Stage 2—15 repeats
  98° C.—15 sec
  72° C.—10 min

Stage 3—72° C. 10 min
  4° C. to storage
  Samples were recovered and analyzed as in Example 1a.

Figure 12:
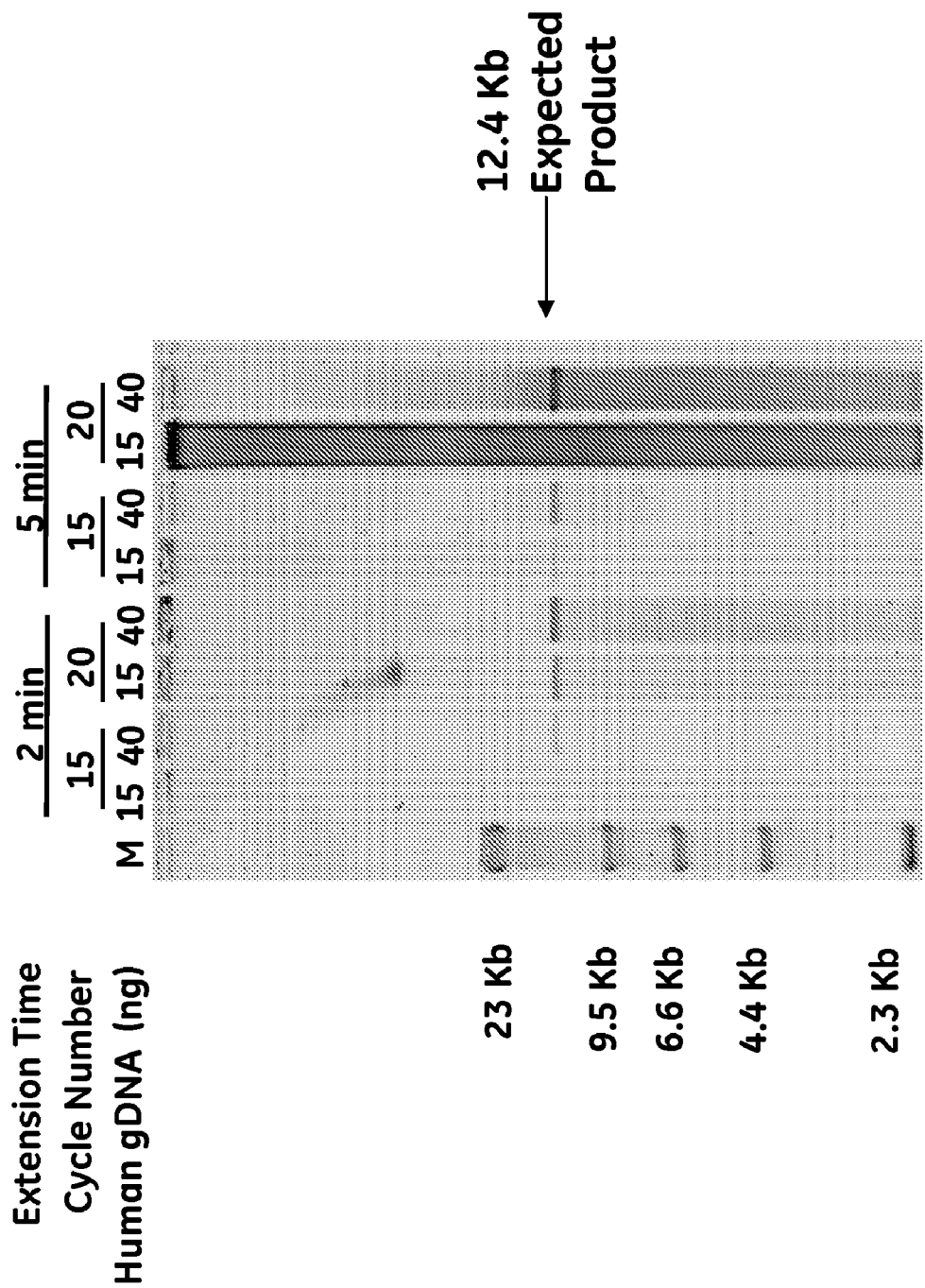
FIG. 12 displays on an agarose electrophoresis gel, the products of an amplification using Tba Exo* DNA polymerase to amplify a 12.4 kb amplicon of mitochondrial DNA present in human genomic DNA. Amounts of human genomic DNA are indicated, as are variations in PCR extension times and number of cycles. The expected product size is indicated. M-DNA marker.

The genome of *Rhodobacter spheroides*, with an average 68% GC content, provides special difficulties in amplification by PCR. Despite this challenge, specific amplicons of 10.4, 10.7 and 14 kb were easily and cleanly amplified out of purified *Rhodobacter spheroides* DNA yielding the expected size product in all conditions tested. Addition of TMSO, thought to enhance the amplification of GC rich templates (Chakrabati R. and Schutt C. E., Biotechniques 32, pp 866-872, 2002), had little or no effect in our system, suggesting that the conditions are sufficient for amplification of these difficult templates, albeit requiring longer amplification times (FIG. 12).

Example 5

Amplification of Mitochondrial DNA Present in Isolated Human DNA

The ability of Tba Exo* DNA polymerase for the amplification of very low concentration targets present in human genomic DNA was tested by evaluating the amplification of a 12.4 kb amplicon of human mitochondrial DNA using human genomic DNA as template. Human genomic DNA contains about 0.1% of mitochondrial DNA (i.e., 15 ng genomic DNA is expected to have around 15 pg of mitochondrial DNA).

Amplification was carried out in a final volume of 25 µl using 15-40 ng of human genomic DNA (Corriell Institute) and containing 25 mM Tricine KOH pH 8.7, 40 mM potassium acetate, 2.4 mM magnesium acetate, 0.02% RE-960, 0.5 mM dATP, 0.5 mM dCTP, 0.5 mM dTTP, 0.5 mM dGTP, 0.4 µM of forward primer MK-7F-11673, 0.4 µM reverse primer MK-7F-11673. Amounts of Human Genomic DNA were varied as indicated. Reactions were assembled on ice followed by addition of 40 ng of Tba Exo* DNA polymerase and initiated by placing in the PCR thermocycler preheated to 94° C.

Cycling was as Follows:

Stage 1—94° C.—1 min

Stage 2—15 or 20 repeats
  94° C.—15 sec
  68° C.—30 sec
  69° C.—2.5 min or 5 min, as indicated Stage 3—72° C. 10 min
  4° C. to storage
  Samples were recovered and analyzed as in Example 1a using 5 ul of the reaction product (FIG. 12). Successful amplification of 12.4 kb mitochondrial amplicon was achieved using as low as 15 ng of human genomic DNA (FIG. 12).

Example 6

Amplification of Long Amplicons from Human Genomic DNA Singly and in Multiplex

Amplification was carried out in a final volume of 25 µl using 50 ng of human genomic DNA prepared from whole human blood using ILLUSTRA™ genomicPrep Midi Flow Kit. The amplification reaction also contains 25 mM Tricine KOH pH 8.7, 40 mM potassium acetate, 2.5 mM magnesium acetate, 0.02% polyoxyethylene nonylphenol ether phosphate methyl ester (Rhodafac RE-960 RhonePoulenc), 0.5 mM dATP, 0.5 mM dCTP, 0.5 mM dTTP, 0.5 mM dGTP. Primers were used at 0.1 µM each of forward primer and reverse primer either singly or multiplexed at the same individual primer concentration. Reactions were assembled on ice followed by addition of 100 ng of Tba Exo* DNA polymerase and initiated by placing in PCR thermocycler preheated to 94° C.

The primers were randomly selected from the web site of Perlegen Sciences Inc., and covers different regions of the genome. They are named using the Perlegen number, followed by the expected product size in kb, and the direction. For example, "94073-11 forward" is Perlegen number 94073, will give an 11 kb product and this is the forward primer. These primers include: (1) on chromosome 13: 94073-11 forward: 5'-AAC CTC ATT CAA TTT GGG CAA GCA TAG-3' (SEQ ID NO: 20) and 94073-11 reverse: 5'-ACC ACT CTA CTT CCG TCG AAT ATA ATA CTG GC-3' (SEQ ID NO: 21); (2) on chromosome 21: 2152-15 forward: 5'-GCT GAC TTT GTA TCA CGG GAG ACC TAG AT-3' (SEQ ID NO: 22) and 2152-15 reverse: 5'-TTC TTA TAA TGT GTT TGC ATA ATG CCA TCG TA-3' (SEQ ID NO: 23); (3) on chromosome 18: 253013-16 forward: 5'-TCA CCA CTT TCC CAA GAC ACG GCT ACA-3' (SEQ ID NO: 24) and 253013-16 reverse: 5'-GCT GCT AGT ACA GGC TCT CGC AAT GAC TAC AC-3' (SEQ ID NO: 25); and (4) on chromosome 18: 247881-19 forward: 5'-GGA TCT TTA GGA ACG CTA TAA CGC CAT TAG GA-3' (SEQ ID NO: 26) and 247881-19 reverse: 5'-CAC TGT GCT GGA GAA GTA GAT AGA ACG CAT TT-3' (SEQ ID NO: 27).

Cycling was as Follows:

Stage 1—94° C.—1 min

Stage 2—20 repeats
  94° C.—15 sec
  68° C.—10 min

Figure 13:
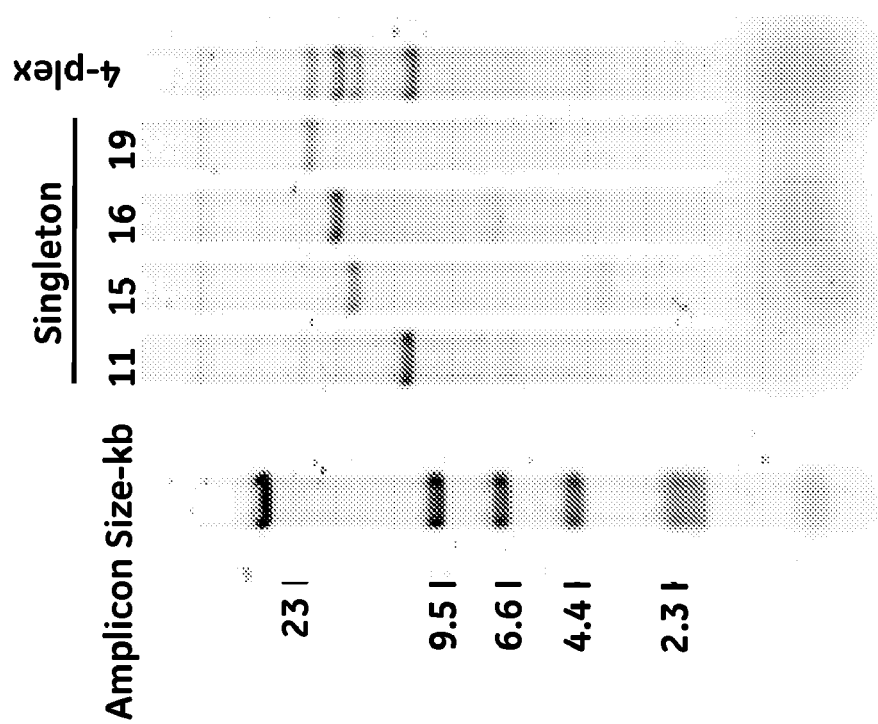
FIG. 13 displays on an agarose electrophoresis gel, the products of an amplification using Tba Exo* DNA polymerase of several amplicons in human genomic DNA both as individual amplifications and in multiplex. The expected product sizes are indicated. M-DNA marker.

Stage 3—68° C. 10 min
  4° C. to storage
  Samples were recovered and analyzed as in Example 1a using 1 µl of the reaction product (FIG. 13).

The activity of Tba Exo* for the amplification of single copy targets in human genomic DNA was tested by evaluating several amplicons of human DNA ranging from 11 kb to 19 kb. The amplicons were taken randomly from primer sets designed by Perlegen Sciences for genotyping in the Phase II HapMap project. The primers tested gave clean amplification of products of the expected sizes. In addition, all four amplicons could be amplified in a multiplex format simply by including all the primers in the PCR reaction. Not only does this demonstrate the ability of Tba Exo* to amplify long stretches of single copy human DNAs from different chromosomes for analysis but also that it has the specificity to perform these amplifications in multiplex.

Example 7

Amplification of Tiled 40 kb Amplicons for the Human CFTR Gene

Amplification was carried out in a final volume of 25 µl using 100 ng of human genomic DNA prepared from whole human blood using ILLUSTRA™ genomicPrep Midi Flow Kit. The amplification reaction also contains 25 mM Tricine KOH pH 8.7, 40 mM potassium acetate, 2.4 mM magnesium acetate, 0.02% polyoxyethylene nonylphenol ether phosphate methyl ester (Rhodafac RE-960 RhonePoulenc), 0.5 mM dATP, 0.5 mM dCTP, 0.5 mM dTTP, 0.5 mM dGTP. 0.1 µM of forward primer, and 0.1 µM reverse primer. Reactions were assembled on ice followed by addition of 100 ng of Tba Exo* DNA polymerase and initiated by placing in the PCR thermocycler preheated to 96° C.

Primers were designed using the web based application GenoFrag (Zakour N. B. et al., Nucleic Acid Research, 32, pp 17-24, 2004), and named according to the expected size of the amplified products. The primer pairs are: 19033 forward: 5'-GCT GTC TAC TTG GGA GTG ATT TGA G-3' (SEQ ID NO: 28) and 19033 reverse: 5'-GGA CCC AAA GCC CAC AAC CTA AAT A-3' (SEQ ID NO: 29); 19247 forward: 5'-CTT GGT CAG TTG GGT GGA TAG TAG T-3' (SEQ ID NO: 30) and 19247 reverse: 5'-GTG GCA GGG TCT ATG ATG GAA CTA A-3' (SEQ ID NO: 31); 19665 forward: 5'-biotin-GGG TCC TAG TGA TGG TAT CTG AAC A-3' (SEQ ID NO: 32) and 19665 reverse: 5'-GAG GGA ACT TAG AGG ATG GGT CAA T-3' (SEQ ID NO: 33); 20441 forward: 5'-TTG GGA GGA TAG GTG ACA GAA GCA T-3' (SEQ ID NO: 34) and 20441 reverse: 5'-TAG GGA AAG AGC AAG AGC GGA CAA T-3' (SEQ ID NO: 35); 20446 forward: 5'-CTC CAT ATC CCA CCC TAA GAA CAA C-3' (SEQ ID NO: 36) and 20446 reverse: 5'-CGC TCA ACT TCC CAT TAC ATC CTA C-3' (SEQ ID NO: 37); and 20514 forward: 5'-TTC CCA GCT CTG CTT TGT GTA GTT G-3' (SEQ ID NO: 38) and 20514 reverse: 5'-GCC TTC CTC TAA CTC TGC CTT CAT A-3' (SEQ ID NO: 39).

Cycling was as Follows:

Stage 1—96° C.—1.5 min

Stage 2—25 repeats
96° C.—15 sec
70° C.—10 min (for 20 kb amplicons) or 20 min (for 40 kb amplicons)

Stage 3—72° C. 10 min
4° C. to storage

Figure 14B:
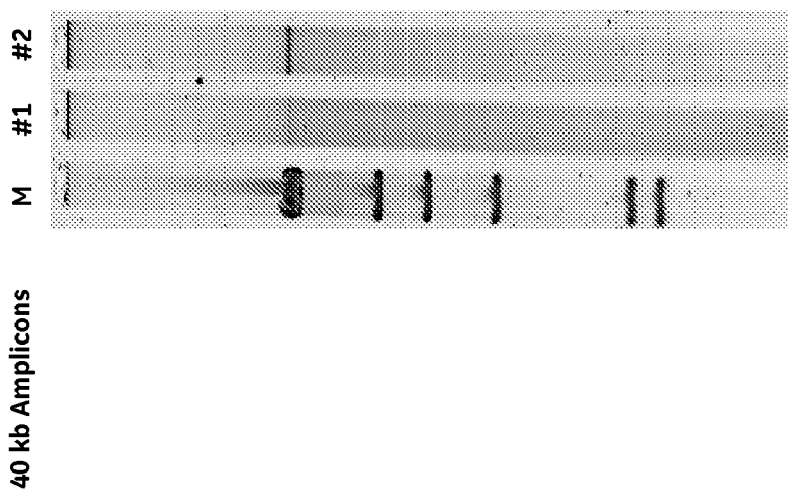
FIGS. 14A and 14B display on agarose electrophoresis gels, the products of amplification using Tba Exo* DNA polymerase of a series of tiled amplicons across the CFTR gene from human genomic DNA.
Figure 14A:
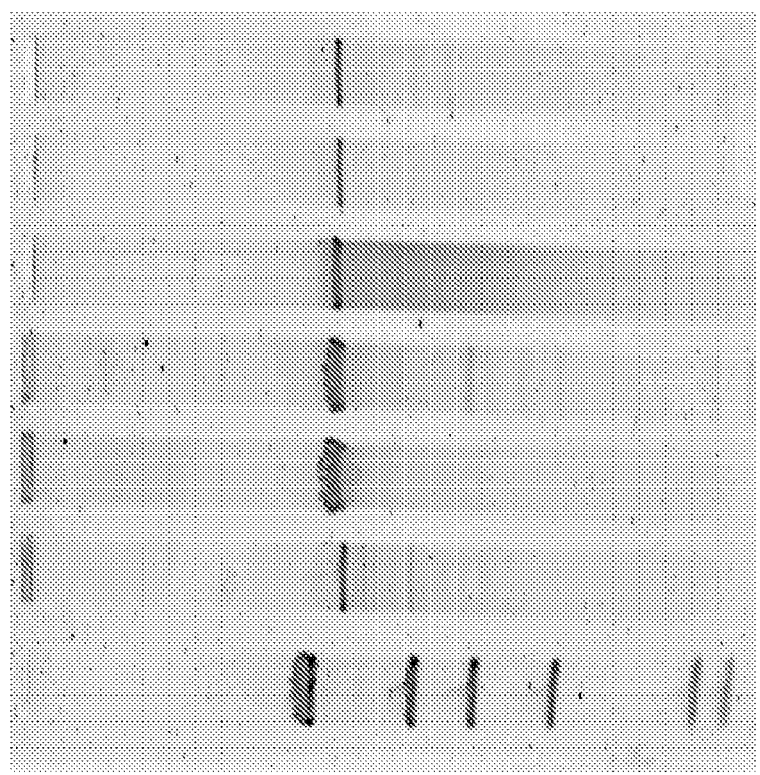

Samples were recovered and analyzed as in Example 1a using 5 µl of the reaction product and run on 0.6% agarose gels to resolve the products (FIG. 14).

Figure 14C:
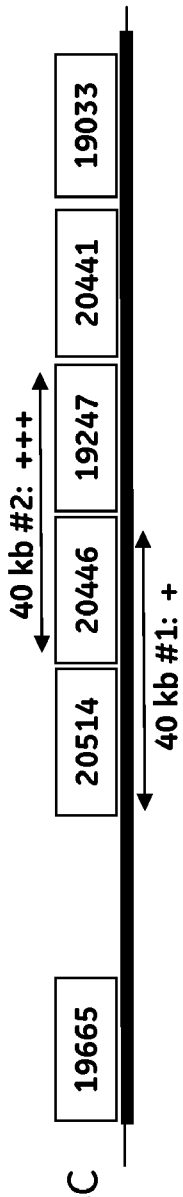
FIG. 14C. Amplicon map of the CFTR gene.

To analyze the structure of a large segment of a gene, tiled 20 kb amplicons were designed across the human CFTR gene (FIG. 14C). A set of these primer pairs was initially amplified to give approximately 20 kb products. Subsequently, alternate primer pairs were used to generate 40 kb amplicons (e.g. 20514 forward with 20446 reverse gave 40 kb #1), thereby amplifying over 80 kb of DNA in 2 reactions, for a total of 60 kb contiguous DNA. Additionally one of the primers was biotinylated for product capture (19665 forward). The ability to repeatably amplify these very long stretches of DNA, coupled with tagging the amplicons with capture labels such as biotin as well as the multiplexing ability as demonstrated in the previous section makes the Tba Exo* based amplification reaction system a powerful tool for genomic analysis.

Although the present invention has been described above in terms of specific embodiments, many modification and variations of this invention can be made as will be obvious to those skilled in the art, without departing from its spirit and scope as set forth in the following claims.

---

What is claimed is:

1. A method for PCR amplification of long nucleic acid target region sequences, which method comprises:
   (a) providing a nucleic acid sample including the amplification target;
   (b) adding oligonucleotide primers, a single thermally stable DNA polymerase of Tba DNA polymerase or Tba exo* DNA polymerase and deoxynucleoside triphosphates to form a reaction mixture; and
   (c) incubating said reaction mixture under thermal cycling conditions to promote amplification of said target by extension of primers to form multiple amplified PCR products using an extension time, in minutes, less than a quarter of the length of the largest PCR product in kb (¼×length of PCR product);
wherein said amplification is performed in the absence of other enzymes or proteins or peptides, and further wherein said amplified PCR product is 10-50 kb in length.

2. The method of claim 1, using an extension time, in minutes, less than one fifth of the length of the largest PCR product in kb (⅕×length of PCR product).

3. The method of claim 1, using an extension time, in minutes, less than one tenth of the length of the largest PCR product in kb (1/10×length of PCR product).

4. The method of claim 1, using an extension time, in minutes, less than one twentieth of the length of the largest PCR product in kb (1/20×length of PCR product).

5. The method of claim 1, wherein said single thermally stable DNA polymerase is Tba DNA polymerase.

6. The method of claim 1, wherein said single thermally stable DNA polymerase is Tba exo* DNA polymerase.

7. The method of claim 1, wherein said primers are exonuclease resistant primers.

8. The method of claim 1, wherein said nucleic acid sample is a low complexity nucleic acid sample.

9. The method of claim 1, wherein said nucleic acid sample is genomic DNA.

10. The method of claim 1, wherein said nucleic acid sample is bacterial or mammalian genomic DNA.

11. The method of claim 1, wherein said nucleic acid sample is human genomic DNA.

12. The method of claim 1, wherein said amplification target has a GC content of 60% or greater.

13. The method of claim 1, wherein said primers include multiple primer pairs for different amplification targets and said reaction produces multiple amplification products.

14. A method for PCR amplification of long nucleic acid target region sequences, which method comprises:
   (a) providing a nucleic acid sample including the amplification target;
   (b) adding oligonucleotide primers, a single thermally stable DNA polymerase of Tba DNA polymerase or Tba exo* DNA polymerase and deoxynucleoside triphosphates to form a reaction mixture; and
   (c) incubating said reaction mixture under thermal cycling conditions to promote amplification of said target by extension of primers to form multiple amplified PCR products;
wherein said amplification is performed in the absence of other enzymes or proteins or peptides, and further wherein said amplified PCR product is 40-50 kb in length.

15. The method of claim 14, wherein said single thermally stable DNA polymerase is Tba DNA polymerase.

16. The method of claim 14, wherein said single thermally stable DNA polymerase is Tba exo* DNA polymerase.

17. A method for synthesizing a complementary strand of a long target nucleic acid molecule, comprising the steps of:
   (a) exposing the target nucleic acid molecule to a complementary primer molecule to effect hybridization of the primer to the target; and
   (b) extending the primer, at high temperature, in the presence of a single thermostable DNA polymerase of Tba DNA polymerase or Tba exo* DNA polymerase and dNTPs under polymerization conditions;
wherein said extension target has a GC content of 60% or greater, said extension is performed in the absence of other enzymes or proteins or peptides, and the extended nucleic acid strand is 40-50 kb in length.

18. The method of claim 17, wherein said single DNA polymerase is Tba DNA polymerase.

19. The method of claim 17, wherein said single DNA polymerase is Tba exo* DNA polymerase.

* * * * *

SEQUENCE LISTING

```
<160> NUMBER OF SEQ ID NOS: 39

<210> SEQ ID NO 1
<211> LENGTH: 778
<212> TYPE: PRT
<213> ORGANISM: Thermococcus barossii

<400> SEQUENCE: 1

Met Ile Leu Asp Val Asp Tyr Ile Thr Glu Asp Gly Lys Pro Val Ile
1               5                   10                  15

Arg Val Phe Lys Lys Asp Lys Gly Glu Phe Lys Ile Glu Tyr Asp Arg
            20                  25                  30

Glu Phe Glu Pro Tyr Ile Tyr Ala Leu Leu Arg Asp Asp Ser Ala Ile
        35                  40                  45

Glu Glu Ile Glu Lys Ile Thr Ala Glu Arg His Gly Lys Val Val Lys
    50                  55                  60

Val Lys Arg Ala Glu Lys Val Lys Lys Lys Phe Leu Gly Arg Ser Val
65                  70                  75                  80

Glu Val Trp Val Leu Tyr Phe Thr His Pro Gln Asp Val Pro Ala Ile
                85                  90                  95

Arg Asp Lys Ile Arg Lys His Pro Ala Val Ile Asp Ile Tyr Glu Tyr
            100                 105                 110
```

```
Asp Ile Pro Phe Ala Lys Arg Tyr Leu Ile Asp Lys Gly Leu Val Pro
        115                 120                 125

Met Glu Gly Asp Glu Glu Leu Lys Leu Met Ser Phe Asp Ile Glu Thr
    130                 135                 140

Leu Tyr His Glu Gly Glu Glu Phe Gly Thr Gly Pro Ile Leu Met Ile
145                 150                 155                 160

Ser Tyr Ala Asp Glu Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Val Ser Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Thr Ala Trp Glu Thr Gly Glu Gly
    290                 295                 300

Leu Glu Arg Val Ala Arg Tyr Ser Met Glu Asp Ala Arg Val Thr Tyr
305                 310                 315                 320

Glu Leu Gly Arg Glu Phe Phe Pro Met Glu Ala Gln Leu Ser Arg Leu
                325                 330                 335

Ile Gly Gln Gly Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Gly Gly Tyr
    370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Lys Ser Tyr Asp
            420                 425                 430

Val Ala Pro Gln Val Gly His Lys Phe Cys Lys Asp Phe Pro Gly Phe
        435                 440                 445

Ile Pro Ser Leu Leu Gly Asn Leu Leu Glu Glu Arg Gln Lys Ile Lys
    450                 455                 460

Arg Lys Met Lys Ala Thr Leu Asp Pro Leu Glu Arg Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Arg Ala Arg Trp Tyr Cys Lys Glu Cys Ala Glu Ser
            500                 505                 510

Val Thr Ala Trp Gly Arg Glu Tyr Ile Glu Met Val Ile Arg Glu Leu
        515                 520                 525
```

```
Glu Glu Lys Phe Gly Phe Lys Val Leu Tyr Ala Asp Thr Asp Gly Leu
    530                 535                 540

His Ala Thr Ile Pro Gly Ala Asp Ala Glu Thr Val Lys Lys Lys Ala
545                 550                 555                 560

Met Glu Phe Leu Asn Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Arg His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Glu Leu Lys Asp
            660                 665                 670

Tyr Lys Ala Thr Gly Pro His Val Ala Ile Ala Lys Arg Leu Ala Ala
        675                 680                 685

Arg Gly Ile Lys Ile Arg Pro Gly Thr Val Ile Ser Tyr Ile Val Leu
690                 695                 700

Lys Gly Ser Gly Arg Ile Gly Asp Arg Ala Ile Pro Phe Asp Glu Phe
705                 710                 715                 720

Asp Pro Thr Lys His Arg Tyr Asp Ala Asp Tyr Tyr Ile Glu Asn Gln
                725                 730                 735

Val Leu Pro Ala Val Glu Arg Ile Leu Arg Ala Phe Gly Tyr Lys Lys
            740                 745                 750

Glu Asp Leu Arg Tyr Gln Lys Thr Arg Gln Val Gly Leu Gly Ala Trp
        755                 760                 765

Leu Gly Met Gly Gly Glu Arg Leu Lys Leu
770                 775

<210> SEQ ID NO 2
<211> LENGTH: 778
<212> TYPE: PRT
<213> ORGANISM: Thermococcus barossii

<400> SEQUENCE: 2

Met Ile Leu Asp Val Asp Tyr Ile Thr Glu Asp Gly Lys Pro Val Ile
1               5                   10                  15

Arg Val Phe Lys Lys Asp Lys Gly Glu Phe Lys Ile Glu Tyr Asp Arg
            20                  25                  30

Glu Phe Glu Pro Tyr Ile Tyr Ala Leu Leu Arg Asp Asp Ser Ala Ile
        35                  40                  45

Glu Glu Ile Glu Lys Ile Thr Ala Glu Arg His Gly Lys Val Val Lys
    50                  55                  60

Val Lys Arg Ala Glu Lys Val Lys Lys Phe Leu Gly Arg Ser Val
65                  70                  75                  80

Glu Val Trp Val Leu Tyr Phe Thr His Pro Gln Asp Val Pro Ala Ile
                85                  90                  95

Arg Asp Lys Ile Arg Lys His Pro Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125
```

```
Met Glu Gly Asp Glu Glu Leu Lys Leu Met Ser Phe Ala Ile Ala Thr
    130                 135                 140

Leu Tyr His Glu Gly Glu Phe Gly Thr Gly Pro Ile Leu Met Ile
145                 150                 155                 160

Ser Tyr Ala Asp Glu Ser Glu Ala Arg Val Ile Thr Trp Lys Lys Ile
                165                 170                 175

Asp Leu Pro Tyr Val Asp Val Val Ser Thr Lys Glu Met Ile Lys
                180                 185                 190

Arg Phe Leu Lys Val Val Lys Glu Lys Asp Pro Asp Val Leu Ile Thr
            195                 200                 205

Tyr Asn Gly Asp Asn Phe Asp Phe Ala Tyr Leu Lys Lys Arg Cys Glu
    210                 215                 220

Lys Leu Gly Val Ser Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
    275                 280                 285

Lys Val Tyr Ala Glu Glu Ile Ala Thr Ala Trp Glu Thr Gly Glu Gly
290                 295                 300

Leu Glu Arg Val Ala Arg Tyr Ser Met Glu Asp Ala Arg Val Thr Tyr
305                 310                 315                 320

Glu Leu Gly Arg Glu Phe Phe Pro Met Glu Ala Gln Leu Ser Arg Leu
                325                 330                 335

Ile Gly Gln Gly Leu Trp Asp Val Ser Arg Ser Ser Thr Gly Asn Leu
                340                 345                 350

Val Glu Trp Phe Leu Leu Arg Lys Ala Tyr Glu Arg Asn Glu Leu Ala
            355                 360                 365

Pro Asn Lys Pro Asp Glu Arg Glu Leu Ala Arg Arg Arg Gly Gly Tyr
    370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Thr His
                405                 410                 415

Asn Val Ser Pro Asp Thr Leu Asn Arg Glu Gly Cys Lys Ser Tyr Asp
                420                 425                 430

Val Ala Pro Gln Val Gly His Lys Phe Cys Lys Asp Phe Pro Gly Phe
            435                 440                 445

Ile Pro Ser Leu Leu Gly Asn Leu Leu Glu Glu Arg Gln Lys Ile Lys
    450                 455                 460

Arg Lys Met Lys Ala Thr Leu Asp Pro Leu Glu Arg Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Arg Ala Arg Trp Tyr Cys Lys Glu Cys Ala Glu Ser
                500                 505                 510

Val Thr Ala Trp Gly Arg Glu Tyr Ile Glu Met Val Ile Arg Glu Leu
            515                 520                 525

Glu Glu Lys Phe Gly Phe Lys Val Leu Tyr Ala Asp Thr Asp Gly Leu
530                 535                 540
```

```
His Ala Thr Ile Pro Gly Ala Asp Ala Glu Thr Val Lys Lys Ala
545                 550                 555                 560

Met Glu Phe Leu Asn Tyr Ile Asn Pro Lys Leu Pro Gly Leu Leu Glu
            565                 570                 575

Leu Glu Tyr Glu Gly Phe Tyr Val Arg Gly Phe Phe Val Thr Lys Lys
        580                 585                 590

Lys Tyr Ala Val Ile Asp Glu Glu Gly Lys Ile Thr Thr Arg Gly Leu
    595                 600                 605

Glu Ile Val Arg Arg Asp Trp Ser Glu Ile Ala Lys Glu Thr Gln Ala
610                 615                 620

Arg Val Leu Glu Ala Ile Leu Arg His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Glu Leu Lys Asp
            660                 665                 670

Tyr Lys Ala Thr Gly Pro His Val Ala Ile Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Thr Lys His Arg Tyr Asp Ala Asp Tyr Tyr Ile Glu Asn Gln
                725                 730                 735

Val Leu Pro Ala Val Glu Arg Ile Leu Arg Ala Phe Gly Tyr Lys Lys
            740                 745                 750

Glu Asp Leu Arg Tyr Gln Lys Thr Arg Gln Val Gly Leu Gly Ala Trp
        755                 760                 765

Leu Gly Met Gly Gly Glu Arg Leu Lys Leu
    770                 775

<210> SEQ ID NO 3
<211> LENGTH: 20
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 3
gctgaagtgg tggaaaccgc                                                   20

<210> SEQ ID NO 4
<211> LENGTH: 22
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 4
acagccaagc ttgcagaaac ga                                                22

<210> SEQ ID NO 5
<211> LENGTH: 22
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 5
```
aacgtgtccg cgcctttgat tt                                    22

<210> SEQ ID NO 6
<211> LENGTH: 24
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 6
tttcctgaca gtgacagact gcgt                                  24

<210> SEQ ID NO 7
<211> LENGTH: 21
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 7
gcctcgcata tcaggaagca c                                     21

<210> SEQ ID NO 8
<211> LENGTH: 20
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 8
cgcgcggtat tgctaacacg                                       20

<210> SEQ ID NO 9
<211> LENGTH: 20
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 9
gattcgccag acgattgaac                                       20

<210> SEQ ID NO 10
<211> LENGTH: 25
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 10
tgccactacc aacgatatga tcggt                                 25

<210> SEQ ID NO 11
<211> LENGTH: 25
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 11
ccgcttcacc ttgaattgct tctac                                 25

<210> SEQ ID NO 12
<211> LENGTH: 19
<212> TYPE: DNA
<213> ORGANISM: ARTIFICIAL SEQUENCE

```
<220> FEATURE:
<223> OTHER INFORMATION: SYNTHETIC OLIGONUCLEOTIDE

<400> SEQUENCE: 12 cccccctgaag cttcaccgg                                                    19

<210> SEQ ID NO 13
<211> LENGTH: 21
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 13
cctacttgcg ctgcatgtgc c                                                  21

<210> SEQ ID NO 14
<211> LENGTH: 25
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 14
ccagcggcgg ggtcaggtgc gttac                                              25

<210> SEQ ID NO 15
<211> LENGTH: 27
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 15
gagccggcga aggtccagga atgtttg                                            27

<210> SEQ ID NO 16
<211> LENGTH: 26
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 16
ggtgctgccg gtgatcgagg agttga                                             26

<210> SEQ ID NO 17
<211> LENGTH: 26
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 17
cgccgcagac gcacccgagg agacac                                             26

<210> SEQ ID NO 18
<211> LENGTH: 25
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 18
ccagcggcgg ggtcaggtgc gttac                                              25
```

<210> SEQ ID NO 19
<211> LENGTH: 24
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 19
ccagaggccg ggcgtgtgat actt                                    24

<210> SEQ ID NO 20
<211> LENGTH: 27
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 20
aacctcattc aatttgggca agcatag                                 27

<210> SEQ ID NO 21
<211> LENGTH: 32
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 21
accactctac ttccgtcgaa tataatactg gc                           32

<210> SEQ ID NO 22
<211> LENGTH: 29
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 22
gctgactttg tatcacggga gacctagat                               29

<210> SEQ ID NO 23
<211> LENGTH: 32
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 23
ttcttataat gtgtttgcat aatgccatcg ta                           32

<210> SEQ ID NO 24
<211> LENGTH: 27
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 24
tcaccacttt cccaagacac ggctaca                                 27

<210> SEQ ID NO 25
<211> LENGTH: 32
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 25
gctgctagta caggctctcg caatgactac ac                    32

<210> SEQ ID NO 26
<211> LENGTH: 32
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 26
ggatctttag gaacgctata acgccattag ga                    32

<210> SEQ ID NO 27
<211> LENGTH: 32
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 27
cactgtgctg gagaagtaga tagaacgcat tt                    32

<210> SEQ ID NO 28
<211> LENGTH: 25
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 28
gctgtctact tgggagtgat ttgag                            25

<210> SEQ ID NO 29
<211> LENGTH: 25
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 29
ggacccaaag cccacaacct aaata                            25

<210> SEQ ID NO 30
<211> LENGTH: 25
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 30
cttggtcagt tgggtggata gtagt                            25

<210> SEQ ID NO 31
<211> LENGTH: 25
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 31
gtggcagggt ctatgatgga actaa                            25

<210> SEQ ID NO 32

```
<211> LENGTH: 25
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 32
gggtcctagt gatggtatct gaaca                                            25

<210> SEQ ID NO 33
<211> LENGTH: 25
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 33
gagggaactt agaggatggg tcaat                                            25

<210> SEQ ID NO 34
<211> LENGTH: 25
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 34
ttgggaggat aggtgacaga agcat                                            25

<210> SEQ ID NO 35
<211> LENGTH: 25
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 35
tagggaaaga gcaagagcgg acaat                                            25

<210> SEQ ID NO 36
<211> LENGTH: 25
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 36
ctccatatcc caccctaaga acaac                                            25

<210> SEQ ID NO 37
<211> LENGTH: 25
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 37
cgctcaactt cccattacat cctac                                            25

<210> SEQ ID NO 38
<211> LENGTH: 25
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 38
```

```
ttcccagctc tgctttgtgt agttg                                         25

<210> SEQ ID NO 39
<211> LENGTH: 25
<212> TYPE: DNA
<213> ORGANISM: ARTIFICIAL SEQUENCE
<220> FEATURE:
<223> OTHER INFORMATION: SYNTHETIC OLIGONUCLEOTIDE

<400> SEQUENCE: 39
gccttcctct aactctgcct tcata                                         25
```